US011078483B1

(12) United States Patent
Kryukov et al.

(10) Patent No.: US 11,078,483 B1
(45) Date of Patent: Aug. 3, 2021

(54) METHODS FOR MEASURING AND IMPROVING CRISPR REAGENT FUNCTION

(71) Applicant: KSQ Therapeutics, Inc., Cambridge, MA (US)

(72) Inventors: Gregory V. Kryukov, Cambridge, MA (US); Michael R. Schlabach, Cambridge, MA (US); Jason J. Merkin, Cambridge, MA (US)

(73) Assignee: KSQ Therapeutics, Inc., Cambridge, MA (US)

( * ) Notice: Subject to any disclaimer, the term of this patent is extended or adjusted under 35 U.S.C. 154(b) by 190 days.

(21) Appl. No.: 15/694,452

(22) Filed: Sep. 1, 2017

Related U.S. Application Data

(60) Provisional application No. 62/383,260, filed on Sep. 2, 2016.

(51) Int. Cl.
| | | |
|---|---|---|
| C40B 50/06 | (2006.01) | |
| C12N 15/11 | (2006.01) | |
| C12N 15/10 | (2006.01) | |
| G16B 20/00 | (2019.01) | |
| G16B 30/00 | (2019.01) | |

(52) U.S. Cl.
CPC .......... *C12N 15/11* (2013.01); *C12N 15/1082* (2013.01); *G16B 20/00* (2019.02); *G16B 30/00* (2019.02); *C12N 2310/20* (2017.05); *C12N 2320/11* (2013.01); *C12N 2330/50* (2013.01); *C40B 50/06* (2013.01)

(58) Field of Classification Search
None
See application file for complete search history.

(56) References Cited

U.S. PATENT DOCUMENTS

| | | |
|---|---|---|
| 8,546,553 B2 | 10/2013 | Terns et al. |
| 8,697,359 B1 | 4/2014 | Zhang et al. |
| 8,771,945 B1 | 7/2014 | Zhang et al. |
| 8,795,965 B2 | 8/2014 | Zhang et al. |
| 8,865,406 B2 | 10/2014 | Zhang et al. |
| 8,871,445 B2 | 10/2014 | Cong et al. |
| 8,889,356 B2 | 11/2014 | Zhang et al. |
| 8,889,418 B2 | 11/2014 | Zhang et al. |
| 8,895,308 B1 | 11/2014 | Zhang et al. |
| 8,901,288 B2 * | 12/2014 | Fellmann ........... C12N 15/1086 536/24.5 |

(Continued)

FOREIGN PATENT DOCUMENTS

| | | |
|---|---|---|
| WO | WO 2007/025097 A2 | 3/2007 |
| WO | WO 2008/021207 A2 | 2/2008 |

(Continued)

OTHER PUBLICATIONS

Chavez et al., "Comparison of Cas9 activators in multiple species." Nature Methods (2016); 13(7): 563-567.

(Continued)

*Primary Examiner* — Christian C Boesen
(74) *Attorney, Agent, or Firm* — Wolf, Greenfield & Sacks, P.C.

(57) ABSTRACT

The invention describes a novel system for identifying optimized gRNAs for use in CRISPR/Cas9 genome editing platforms. The invention allows for the determination of specific gene alterations rendered by a particular gRNA, thereby permitting the generation of optimized gRNA libraries.

22 Claims, 15 Drawing Sheets

Specification includes a Sequence Listing.

(56) References Cited

U.S. PATENT DOCUMENTS

| | | |
|---|---|---|
| 8,906,616 B2 | 12/2014 | Zhang et al. |
| 8,906,682 B2 | 12/2014 | June et al. |
| 8,932,814 B2 | 1/2015 | Cong et al. |
| 8,945,839 B2 | 2/2015 | Zhang et al. |
| 8,993,233 B2 | 3/2015 | Zhang et al. |
| 8,999,641 B2 | 4/2015 | Zhang et al. |
| 9,637,739 B2 | 5/2017 | Virginijus et al. |
| 9,790,490 B2 | 10/2017 | Zhang et al. |
| 9,822,372 B2 | 11/2017 | Zhang et al. |
| 9,834,791 B2 | 12/2017 | Zhang et al. |
| 9,840,713 B2 | 12/2017 | Zhang et al. |
| 9,855,297 B2 | 1/2018 | Duchateau et al. |
| 9,890,393 B2 | 2/2018 | Duchateau et al. |
| 2010/0076057 A1 | 3/2010 | Sontheimer et al. |
| 2010/0093617 A1 | 4/2010 | Barrangou et al. |
| 2010/0257638 A1 | 10/2010 | Cai et al. |
| 2011/0217739 A1 | 9/2011 | Terns et al. |
| 2011/0300538 A1 | 12/2011 | Barrangou et al. |
| 2012/0149115 A1 | 6/2012 | Kim et al. |
| 2012/0277120 A1 | 11/2012 | Serber et al. |
| 2013/0011828 A1 | 1/2013 | Barrangou et al. |
| 2013/0288251 A1 | 10/2013 | Horvath et al. |
| 2014/0068797 A1 | 3/2014 | Doudna et al. |
| 2014/0179770 A1 | 6/2014 | Zhang et al. |
| 2014/0186843 A1 | 7/2014 | Zhang et al. |
| 2014/0186916 A1 | 7/2014 | Allen et al. |
| 2014/0189896 A1 | 7/2014 | Zhang et al. |
| 2014/0242664 A1 | 8/2014 | Zhang et al. |
| 2014/0242699 A1 | 8/2014 | Zhang et al. |
| 2014/0273230 A1 | 9/2014 | Chen et al. |
| 2014/0273233 A1 | 9/2014 | Chen et al. |
| 2014/0310830 A1 | 10/2014 | Zhang et al. |
| 2014/0357530 A1 | 12/2014 | Zhang et al. |
| 2015/0020223 A1 | 1/2015 | Zhang et al. |
| 2015/0031134 A1 | 1/2015 | Zhang et al. |
| 2015/0058069 A1 | 2/2015 | Chavda et al. |
| 2015/0184139 A1 | 7/2015 | Zhang et al. |
| 2015/0203872 A1 | 7/2015 | Zhang et al. |
| 2015/0240261 A1 | 8/2015 | Siksnys et al. |
| 2015/0284727 A1 | 10/2015 | Kim et al. |
| 2015/0291961 A1 | 10/2015 | Siksnys et al. |
| 2015/0322457 A1 | 11/2015 | Kim et al. |
| 2015/0344912 A1 | 12/2015 | Kim et al. |
| 2016/0017366 A1 | 1/2016 | Chen et al. |
| 2016/0046961 A1 | 2/2016 | Jinek et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0102324 A1 | 4/2016 | Duchateau et al. |
| 2016/0115488 A1 | 4/2016 | Zhang et al. |
| 2016/0115489 A1 | 4/2016 | Zhang et al. |
| 2016/0120905 A1 | 5/2016 | Galetto et al. |
| 2016/0122774 A1 | 5/2016 | Duchateau et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0145645 A1 | 5/2016 | Bahr et al. |
| 2016/0184362 A1 | 6/2016 | Duchateau et al. |
| 2016/0272965 A1* | 9/2016 | Zhang ............... C12N 15/1082 |
| 2016/0272999 A1 | 9/2016 | Duchateau et al. |
| 2016/0281072 A1 | 9/2016 | Zhang et al. |
| 2016/0298096 A1 | 10/2016 | Charpentier et al. |
| 2016/0340662 A1 | 11/2016 | Zhang et al. |
| 2017/0016025 A1 | 1/2017 | Poirot et al. |
| 2017/0051310 A1 | 2/2017 | Doudna et al. |
| 2017/0051312 A1 | 2/2017 | Jinek et al. |
| 2017/0051354 A1 | 2/2017 | Davis et al. |
| 2017/0107536 A1 | 4/2017 | Zhang et al. |
| 2017/0152528 A1 | 6/2017 | Zhang et al. |
| 2017/0166893 A1 | 6/2017 | Doudna et al. |
| 2017/0175142 A1 | 6/2017 | Zhang et al. |
| 2017/0191078 A1 | 7/2017 | Zhang et al. |
| 2017/0191123 A1 | 7/2017 | Kim et al. |

FOREIGN PATENT DOCUMENTS

| | | |
|---|---|---|
| WO | WO 2010/011961 A2 | 1/2010 |
| WO | WO 2010/054108 A2 | 5/2010 |
| WO | WO 2010/054154 A2 | 5/2010 |
| WO | WO 2012/054726 A1 | 4/2012 |
| WO | WO 2012/149470 A1 | 11/2012 |
| WO | WO 2012/164565 A1 | 12/2012 |
| WO | WO 2013/098244 A1 | 7/2013 |
| WO | WO 2013/126794 A1 | 8/2013 |
| WO | WO 2013/141680 A1 | 9/2013 |
| WO | WO 2013/142578 A1 | 9/2013 |
| WO | WO 2013/176772 A1 | 11/2013 |
| WO | WO 2014/089290 A1 | 6/2014 |
| WO | WO 2014/093661 A2 | 6/2014 |
| WO | WO 2014/093701 A1 | 6/2014 |
| WO | WO 2014/093718 A1 | 6/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/204727 A1 | 12/2014 |
| WO | WO 2014/205192 A2 | 12/2014 |
| WO | WO 2015/071474 A2 | 5/2015 |
| WO | WO 2015/075175 A1 | 5/2015 |
| WO | WO 2015/075195 A1 | 5/2015 |
| WO | WO 2015/089351 A1 | 6/2015 |
| WO | WO 2015/089427 A1 | 6/2015 |
| WO | WO 2015/155341 A1 | 10/2015 |
| WO | WO 2015/161276 A2 | 10/2015 |
| WO | WO 2015/167959 A1 | 11/2015 |
| WO | WO 2016/094872 A1 | 6/2016 |
| WO | WO 2016/094874 A1 | 6/2016 |
| WO | WO 2016/094880 A1 | 6/2016 |
| WO | WO 2016/100974 A1 | 6/2016 |
| WO | WO 2016/205613 A1 | 12/2016 |
| WO | WO 2016/210271 A1 | 12/2016 |
| WO | WO 2017/053762 A1 | 3/2017 |
| WO | WO 2017/079673 A1 | 5/2017 |
| WO | WO 2017/120546 A1 | 7/2017 |
| WO | WO 2017/123609 A1 | 7/2017 |
| WO | WO 2017/209809 A1 | 12/2017 |
| WO | WO 2018/035387 A1 | 2/2018 |
| WO | WO 2018/035388 A1 | 2/2018 |

OTHER PUBLICATIONS

Cleary et al., "Production of complex nucleic acid libraries using highly parallel in situ oligonucleotide synthesis." Nature Methods (2004); 1(3): 241-247.

Cooper et al., "Highly efficient large-scale lentiviral vector concentration by tandem tangential flow filtration." Journal of Virological Methods (2011); 177(1): 1-9.

Davis et al., "Small molecule-triggered Cas9 protein with improved genome-editing specificity." Nature Chemical Biology (2015); 11(5): 316-318.

Doench et al., "Optimized sgRNA design to maximize activity and minimize off-target effects of CRISPR-Cas9." Nature Biotechnology (2016); 34: 184-191.

Doench et al., "Rational design of highly active sgRNAs for CRISPR-Cas9-mediated gene inactivation." Nature Biotechnology (2014); 32(12): 1262-1267.

Dominguez et al., "Beyond editing: repurposing CRISPR-Cas9 for precision genome regulation and interrogation." Nature Reviews Molecular Cell Biology (2016); 17(1): 5-15.

Dow et al., "Inducible in vivo genome editing with CRISPR-Cas9." Nature Biotechnology (2015); 33: 390-394.

Geraerts et al., "Upscaling of lentiviral vector production by tangential flow filtration." The Journal of Gene Medicine (2005); 7(10): 1299-1310.

Gilbert et al., "Genome-Scale CRISPR-Mediated Control of Gene Repression and Activation." Cell (2014); 159(3): 647-661.

Henriksen et al., "Comparison of RNAi efficiency mediated by tetracycline-responsive H1 and U6 promoter variants in mammalian cell lines." Nucleic Acids Research (2007); 35(9): e67.

Jiang et al., "An optimized method for high-titer lentivirus preparations without ultracentrifugation." Scientific Reports (2015); 5: 13875.

(56) References Cited

OTHER PUBLICATIONS

Konermann et al., "Genome-scale transcriptional activation by an engineered CRISPR-Cas9 complex." Nature (2015); 517(7536): 583-588.
Ma et al., "A CRISPR-Based Screen Identifies Genes Essential for West-Nile-Virus-Induced Cell Death." Cell Reports (2015); 12(4): 673-683.
Moreno-Mateos et al., "CRISPRscan: designing highly efficient sgRNAs for CRISPR-Cas9 targeting in vivo." Nature Methods (2015); 12(10): 982-988.
Rey-Giraud et al., "In Vitro Generation of Monocyte-Derived Macrophages under Serum-Free Conditions Improves Their Tumor Promoting Functions." PLoS One (2012); 7(8): e42656.
Schumann et al., "Generation of knock-in primary human T cells using Cas9 ribonucleoproteins." PNAS (2015); 112(33): 10437-10442.
Sternberg and Doudna, "Expanding the Biologist's Toolkit with CRISPR-Cas9." Molecular Cell (2015); 58(4): 568-574.
Tiscornia et al., "Production and purification of lentiviral vectors." Nature Protocols (2006); 1(1): 241-245.
Wang et al., "Genetic Screens in Human Cells Using the CRISPR-Cas9 System." Science (2014); 343(6166): 80-84.
Wang et al., "Identification and characterization of essential genes in the human genome." Science (2015); 350(6264): 1096-1101.
Wucherpfennig et al., "Genetic screens to study the immune system in cancer." Current Opinion in Immunology (2016); 41:55-61.
Zhang et al., "A CRISPR screen defines a signal peptide processing pathway required by flaviviruses." Nature (2016); 535(7610): 164-168.
Zhang et al., "A more efficient RNAi inducible system for tight regulation of gene expression in mammalian cells and xenograft animals." RNA (2007); 13: 1375-1383.

\* cited by examiner

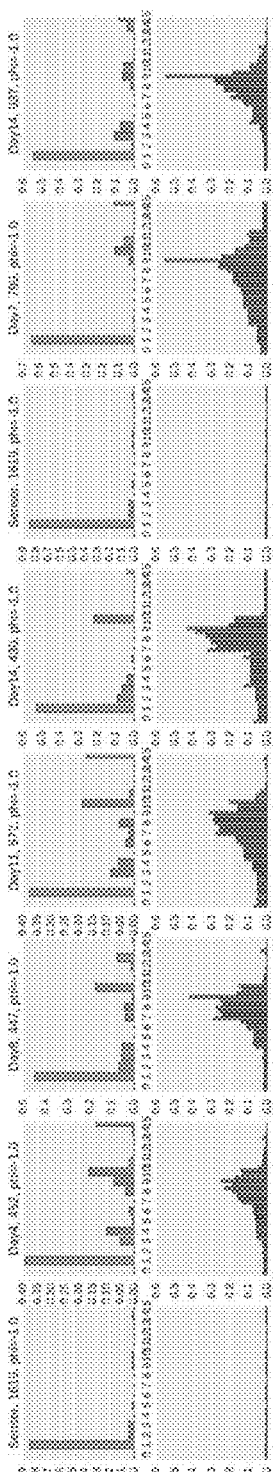
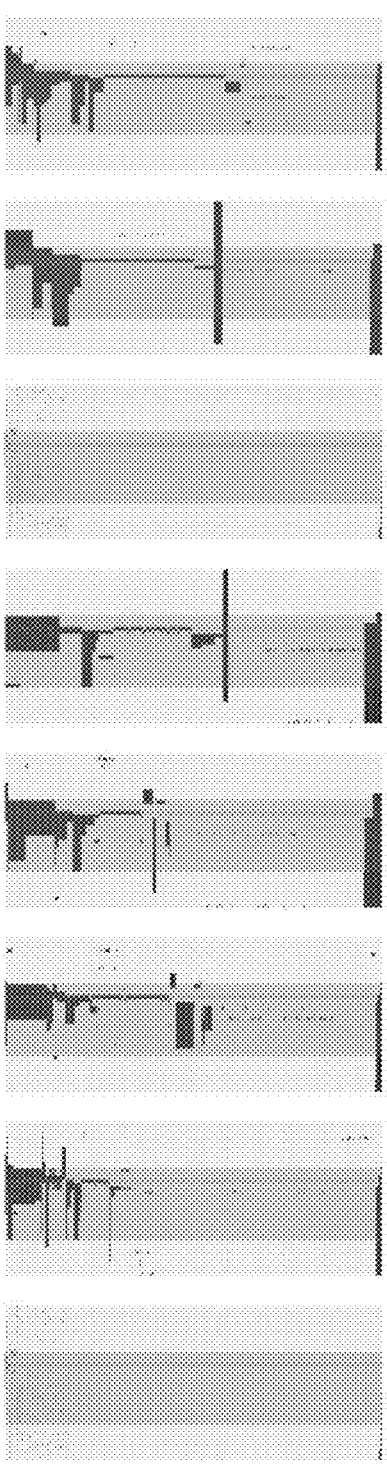
FIG. 3A prop. of cuts
FIG. 3B frac cut
FIG. 3C reads

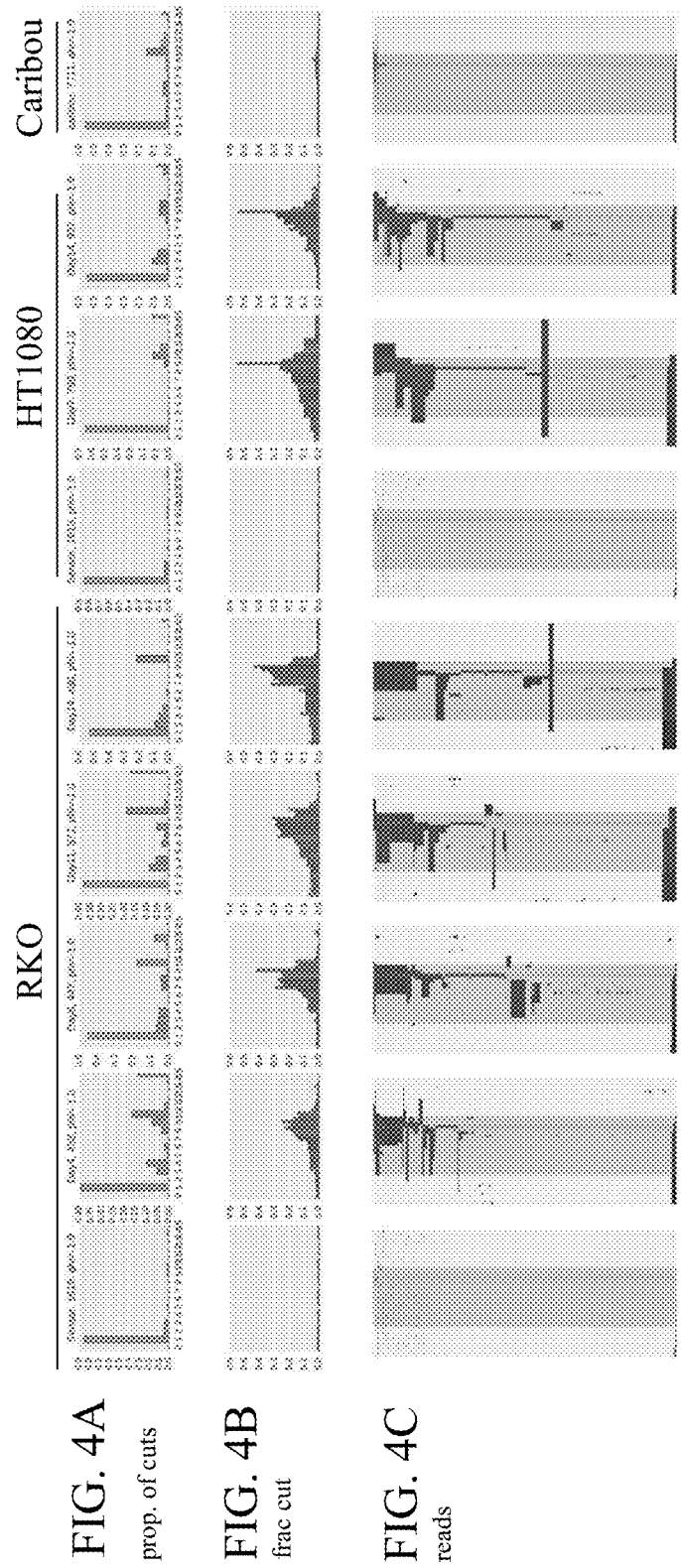
FIG. 4A prop. of cuts
FIG. 4B frac cut
FIG. 4C reads

FIG. 14
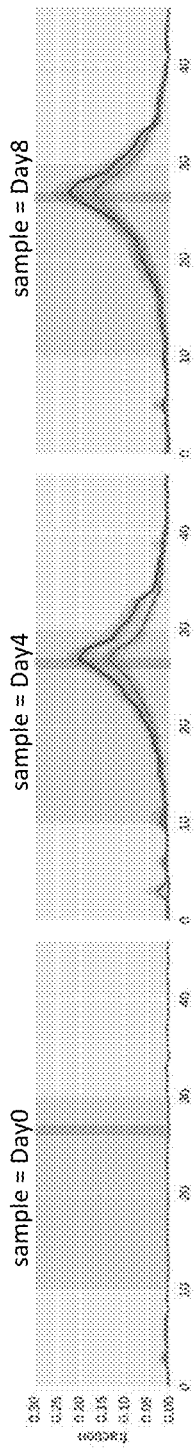
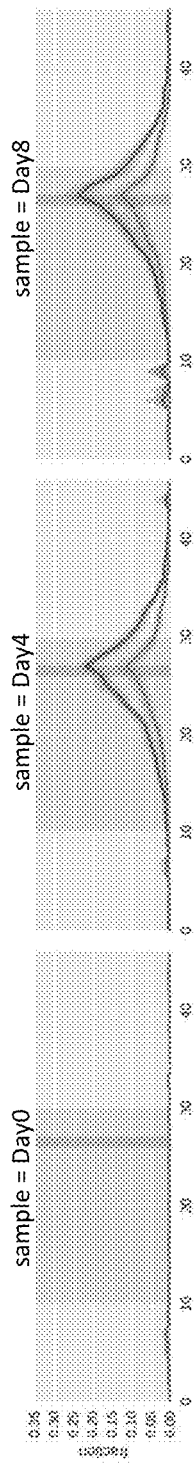
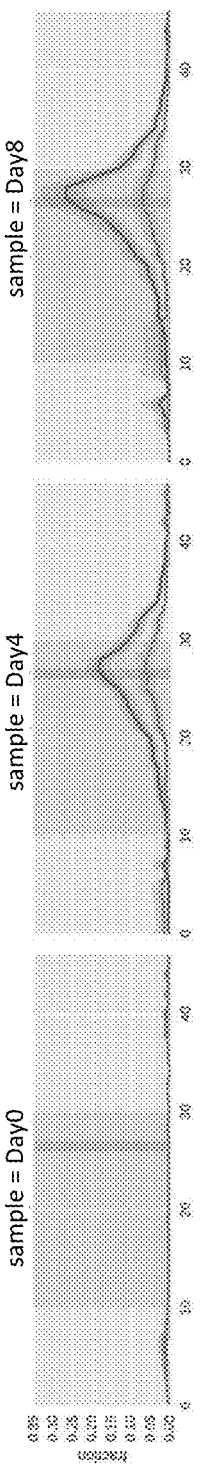

METHODS FOR MEASURING AND IMPROVING CRISPR REAGENT FUNCTION

DESCRIPTION OF RELATED APPLICATIONS

This application claims priority to U.S. Provisional Application No. 62/383,260, filed Sep. 2, 2016, the contents of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: KQST_003_01US_ST25.txt, date recorded: Aug. 29, 2017, file size: 29 kilobytes).

FIELD OF THE INVENTION

The present invention relates to the high-throughput evaluation of the efficacy of functional genomics reagents. Specifically, evaluation of specific genetic alterations that result from Cas9-targeting to a target sequence by a specific guide RNA (gRNA) can be performed simultaneously for large numbers of single guide RNAs (sgRNAs) in a high-throughput manner. Additionally, libraries of gRNAs that are optimized for a particularly desired type of genetic alteration are provided.

BACKGROUND OF THE INVENTION

Nucleic acid libraries have been constructed using biologically derived or chemically synthesized nucleic acids as substrates. Methods have been developed for the purpose of generating complex, and hence, comprehensive, libraries which are useful for functional analysis of genomes. For example, Cleary et al. (2004) Nature Methods 1: 241-247 discloses complex libraries of defined nucleic acids developed in order to create large-scale libraries of short hairpin RNAs (shRNAs) targeting numerous human and mouse genes.

In the past decade, use of clustered regularly interspaced short palindromic repeats (CRISPR) gene editing technology has sparked a revolution in the biological sciences. CRISPR site-specific editing in eukaryotic cells has been used for the gene modification in many plant and animal models. Sternberg and Doudna (2015) Molecular Cell 58: 568-574, describe the development and use of CRISPR-Cas9 for such diverse applications as genome editing, gene regulation, and genome-wide screening systems.

Although libraries of guide RNAs have been reported, use of the CRISPR-Cas9 system in genome-wide screening systems has demonstrated that many guide RNAs either fail to result in editing of the designated target or result in editing of the designated target in an undesired manner. Empirical studies have identified gRNA determinants that can influence the efficacy of Cas9 (Moreno-Mateos et al, Nature Methods, v. 12, pp. 982-988, (2015)). Additional studies aimed at identifying functional gRNAs have resulted in the generation of predictive algorithms for the improvement of guide RNA design (Doench et al, Nature Biotechnology, v. 32, pp. 1262-1267, (2014)). However, such algorithms are suboptimal, as a significant number of guides identified by such algorithms still fail to result in the desired gene editing, or result in less optimal editing than other guides directed against the same target locus. Further, these non-functional or hypo-functional gRNAs increase the expense and difficulty of performing genetic screens with the CRISPR-Cas9 system.

As such, there is a need in the art for methods of identifying optimal guide RNAs that result in specific and predictable genetic modifications.

SUMMARY OF THE INVENTION

The present invention provides a novel platform for identification of guide RNAs (gRNAs) that result in optimal gene editing, and for generation of optimized gRNA libraries that are useful for discovery, research and development. Specifically, a library of unique nucleic acid constructs comprising a gRNA and the corresponding gRNA target sequence is utilized in a high-throughput manner to identify gRNAs that result in specific gene modifications in the context of the CRISPR-Cas9 system. Prior to this invention, methods for selecting gRNAs were primarily limited to suboptimal predictive algorithms that often failed to predict gRNA efficacy, or functional analysis of a relatively small number of gRNAs. Further, none of these prior methods provide detailed information on the nature of the resultant genetic modification (e.g. the presence or absence of a frameshift mutation, the size of insertions or deletions resulting in these frameshift mutations, or the mechanism by which the DNA was repaired).

In some embodiments, the present invention provides a method of preparing an optimized guide RNA (gRNA) library comprising; (a) introducing a library of nucleic acid constructs, into a population of cells modified to express a Cas9 protein, wherein each construct comprises a gRNA sequence and a sensor sequence, wherein the sensor sequence comprises the corresponding gRNA target sequence; (b) culturing said cells from step (a) under conditions permitting the expression of said gRNA and said Cas9 protein; (c) amplifying the nucleic acid constructs sequences by polymerase chain reaction (PCR) from the cells of step (b) to obtain a plurality of amplicons, wherein each amplicon comprises the gRNA sequence and a the sensor sequence; (d) sequencing said plurality of amplicons; (e) determining a pattern of alterations in the sensor sequence in each of the amplicons; and (f) identifying a population of gRNAs that produce a desired pattern of alterations in the sensor sequence. In some embodiments, the library of nucleic acid constructs encode a genome wide or a sub-genome wide library of gRNAs.

In some embodiments, the population of cells is modified with a nucleic acid encoding a Cas9 protein. In some embodiments, the nucleic acid encoding a Cas9 protein is DNA. In some embodiments, the nucleic acid encoding a Cas9 protein is mRNA. In some embodiments, the mRNA is introduced into the population of cells by electroporation. In some embodiments, the nucleic acid encoding a Cas9 protein is encoded by a viral vector. In some embodiments, the viral vector is a lentiviral vector. In some embodiments, the lentiviral vector is introduced at a titer of at least about $1 \times 10^6$ infectious particles/mL. In some embodiments, the lentiviral vector is introduced at a titer of at least about $1 \times 10^7$ infectious particles/mL.

In some embodiments, the Cas9 protein is a dCas9 protein. In some embodiments, the dCas9 protein is fused with a transcriptional repressor domain. In some embodiments, the repressor domain is selected from the group consisting of MAX-interacting protein 1 (MXI1), Krüppel-associated box (KRAB) domain, and four contancenated mSin3 domains (SID4X). In some embodiments, the dCas9 protein is fused with a transcriptional activator. In some embodiments, the transcriptional activator is selected from the group consisting of one or multiple repeats of the herpes simplex VP16 activation domain (VP64 or VP160) and the nuclear factor kB (NK-κB) transactivating subunit activation domain (p65AD). In some embodiments, the dCas9 protein is fused with a heterologous protein domain. In some embodiments, the heterologous enzymatic domain is cytidine deaminase.

In some embodiments, the Cas9 protein is fused with a heterologous enzymatic domain. In some embodiments, the heterologous enzymatic domain is selected from the group consisting of an exonuclease and a phosphatase.

In some embodiments, the Cas9 protein is a nickase mutant of Cas9. In some embodiments, the Cas9 protein is derived from *Staphylococcus aureus* (SaCas9). In some embodiments, the Cas9 protein is derived from *Streptococcus pyogenes* (SpCas9).

In some embodiments, the expression of the nucleic acid encoding a Cas9 protein is under the control of an inducible gene element. In some embodiments, the nucleic acid encoding a Cas9 protein further encodes a selectable marker. In some embodiments, the selectable marker is a fluorophore or an antibiotic resistance gene.

In some embodiments, the population of cells are mammalian cells. In some embodiments, the mammalian cells are human cells or non-human cells. In some embodiments, the sensor sequence is a nucleic acid sequence derived from a mammalian genome. In some embodiments, the mammalian genome is a human genome or a non-human genome. In some embodiments, the sensor sequence is derived from a human genome and the gRNAs produce the desired pattern of alterations in the human sensor sequence and also produce the desired pattern of alterations in a non-human sensor sequence. In some embodiments, the sensor sequence is derived from a non-human genome and the gRNAs produce the desired pattern of alterations in the non-human sensor sequence and also produce the desired pattern of alterations in a human sensor sequence.

In some embodiments, the nucleic acid construct is encoded by a viral vector. In some embodiments, the viral vector is a lentiviral vector. In some embodiments, the lentiviral vector is introduced at a titer of at least about $1 \times 10^6$ infectious particles/mL. In some embodiments, the lentiviral vector is introduced at a titer of at least about $1 \times 10^7$ infectious particles/mL. In some embodiments, the nucleic acid construct is under the control of an inducible gene element.

In some embodiments, the sequencing comprises high throughput sequencing. In some embodiments, the sequencing is performed at a sequencing depth of at least 100 reads/amplicon. In some embodiments, the sequencing is performed at a sequencing depth of between 100 and 250 reads/amplicon. In some embodiments, the sequencing is performed at a sequencing depth of about 150 reads/amplicon.

In some embodiments, the desired pattern of alterations is selected from a group consisting of insertions in the sensor sequence, deletions in the sensor sequence, and mutations in the sensor sequence.

In some embodiments, the methods of the present invention further comprise introducing a nucleic acid sequence encoding a repair template into the transduced population of cells. In some embodiments, the desired pattern of alterations comprises insertion of at least a portion of the repair template into a specific site of the sensor sequence. In some embodiments, at least 90% of the repair template is inserted into the specific site of the sensor sequence. In some embodiments, at least 95% of the repair template is inserted into the specific site of the SENSR™ sequence. In some embodiments, at least 97% of the repair template is inserted into the specific site of the sensor sequence. In some embodiments, at least 99% of the repair template is inserted into the specific site of the sensor sequence. In some embodiments, 100% of the repair template is inserted into the specific site of the sensor sequence.

In some embodiments, the desired pattern of alterations does not comprise deletions in the sensor sequence, mutations in the sensor sequence, or insertions in the sensor sequence other than the insertion of the repair template nucleic acid sequence.

In some embodiments, the desired pattern of alterations are a result of a mechanism selected from the group consisting of non-homologous end-joining (NHEJ) and homology-directed repair (HDR).

In some embodiments, the library of nucleic acid constructs is introduced into the cells prior to the nucleic acid encoding Cas9. In some embodiments, the library of nucleic acid constructs and the nucleic acid encoding Cas9 are introduced into the cells at substantially the same time. In some embodiments, the method is performed in vitro or in vivo.

In some embodiments, the methods of the present invention further comprise amplifying an endogenous target nucleic acid sequence by PCR from the cells to obtain a plurality of endogenous target amplicons; sequencing said endogenous target amplicons; determining a pattern of alterations in said endogenous target sequence; comparing the pattern of alterations in the endogenous target sequence with the pattern of alterations in the sensor sequence; and determining a population of gRNAs that produce a desired pattern of alterations in both the endogenous target sequence and the sensor sequence. In some embodiments, the desired pattern of alterations in the endogenous target sequence and the sensor sequence are substantially similar.

In some embodiments, the methods of the present invention further comprise quantifying a transcription level of an endogenous target sequence and/or sensor sequence from the population of cells by quantitative PCR (qPCR); comparing the transcription level to a transcription level of the endogenous target sequence and/or sensor sequence obtained from a control cell population by qPCR; determining a pattern of transcriptional changes in the endogenous target sequence and/or sensor sequence; and determining a population of gRNAs that produce a desired pattern of transcriptional changes in the endogenous target sequence and/or sensor sequence. In some embodiments, the desired pattern of transcriptional changes are selected from the group consisting of increased transcription of the endogenous target sequence and/or sensor sequence relative to the control cell population, decreased transcription of the endogenous target sequence and/or sensor sequence relative to the control cell population, and increased or decreased expression of a reporter protein.

In some embodiments, the present invention provides an optimized guide RNA (gRNA) library prepared by: (a) introducing a library of nucleic acid constructs, into a population of cells modified to express a Cas9 protein, wherein each construct comprises a gRNA sequence and a sensor sequence, wherein the sensor sequence comprises the corresponding gRNA target; (b) culturing said cells from step (a) under conditions permitting the expression of said gRNA and said Cas9 protein; (c) amplifying the nucleic acid construct sequences by polymerase chain reaction (PCR)

from the cells of step (b) to obtain a plurality of amplicons, wherein each amplicon comprises a gRNA nucleic acid sequence and a sensor sequence; (d) sequencing said plurality of amplicons; (e) determining a pattern of alterations in the sensor sequence in each of said amplicons; and (f) identifying a population of optimized gRNAs that produce a desired pattern of alterations in said sensor sequence; and (g) preparing a library of said optimized gRNAs.

In some embodiments, the desired pattern of alterations is selected from the group consisting of insertions in the sensor sequence, deletions in the sensor sequence, and mutations in the sensor sequence.

In some embodiments, methods of preparing an optimized gRNA library further comprise amplifying an endogenous target nucleic acid sequence by PCR from the cells to obtain a plurality of endogenous target amplicons; sequencing said endogenous target amplicons; determining a pattern of alterations in said endogenous target sequence; comparing the pattern of alterations in the endogenous target sequence with the pattern of alterations in the sensor sequence; and identifying a population of gRNAs that produce a desired pattern of alterations in both the endogenous target sequence and the sensor sequence. In some embodiments, the desired pattern of alterations in the endogenous target sequence and the sensor sequence are substantially similar.

In some embodiments, methods of preparing an optimized gRNA library further comprise quantifying a transcription level of an endogenous target sequence from the population of cells by quantitative PCR (qPCR); comparing the transcription level to a transcription level of the endogenous target sequence obtained from a control cell population by qPCR; determining a pattern of transcriptional changes in the endogenous target sequence; and identifying a population of gRNAs that produce a desired pattern of transcriptional changes in the endogenous target sequence. In some embodiments, the desired pattern of transcription changes are selected from the group consisting of increased transcription of the endogenous target sequence relative to the control cell population and decreased transcription of the endogenous target sequence relative to the control cell population.

In some embodiments, the optimized gRNA library is genome-wide. In some embodiments, the optimized gRNA library is subgenome-wide. In some embodiments, the subgenome-wide library is targeted to genes associated with a given disease or disorder. In some embodiments, the disease or disorder is selected from the group consisting of inflammatory diseases, autoimmune diseases, asthma, and cancer. In some embodiments, the subgenome-wide library is targeted to genes encoding a cell surface receptor. In some embodiments, the subgenome-wide library is targeted to genes identified in drug-combination or small molecule studies. In some embodiments, the optimized gRNA library comprises high-fidelity gRNAs. In some embodiments, the high-fidelity gRNAs result in a mutant-specific pattern of alterations or pattern of transcriptional changes. In some embodiments, the high-fidelity gRNAs target a disease-specific allele.

In some embodiments, the present invention provides methods of detecting the presence of one or more single nucleotide polymorphisms (SNPs) comprising: (a) introducing an optimized gRNA library comprised of high-fidelity gRNAs into a population of cells that have been modified to express Cas9; (b) culturing said cells from step (a) under conditions permitting the expression of said gRNA and said Cas9 protein; (c) amplifying gRNA target sequences by polymerase chain reaction (PCR) from the cells of step (b) to obtain a plurality of target amplicons; (d) sequencing said plurality of target amplicons; (e) detecting the presence of genetic alterations within the target sequence; and (f) determining the presence of one or more SNPs based on the presence of genetic alterations within the target sequence, or in adjoining sequences such as the protospacer adjacent motif (PAM).

In some embodiments, the present invention provides methods of predicting the performance of a gRNA in a mammalian cell system comprising; (a) introducing a library of nucleic acid constructs, into a population of cells modified to express a Cas9 protein, wherein each construct comprises a gRNA sequence and a sensor sequence, wherein the sensor sequence comprises the corresponding gRNA target sequence; (b) culturing said cells from step (a) under conditions permitting the expression of said gRNA and said Cas9 protein; (c) amplifying the nucleic acid constructs sequences by polymerase chain reaction (PCR) from the cells of step (b) to obtain a plurality of amplicons, wherein each amplicon comprises the gRNA sequence and a the sensor sequence; (d) sequencing said plurality of amplicons; (e) determining a pattern of alterations in the sensor sequence in each of the amplicons; (f) identifying a first population of gRNAs that produce a desired pattern of alterations in the sensor sequence and identifying a second population of gRNAs that do not produce the desired pattern of alteration in the sensor sequence; (g) analyzing one or more features of the first and second population of gRNAs to determine a pattern of features for each of the first and second populations of gRNAs; (h) generating a model to predict gRNA performance based on of the pattern of features of the first and second populations of gRNAs; (i) applying the model of (h) to one or more gRNAs that are not present in either the first or second population of gRNAs in step (f), wherein the model is capable of identifying one or more gRNAs that are not present in either the first or second population of gRNAs that will result in the desired pattern of alterations.

In some embodiments, the one or more features are selected from the group consisting of gRNA melting temperature, gRNA CG content, the purine content of the gRNA, the pyrimidine content of the gRNA, the genomic context of the gRNA target site, the identity of nucleotides present at one or more positions in the gRNA. In some embodiments, the analyzingcomprises analyzing a specific range of nucleotide positions in the gRNA. In some embodiments, the range of nucleotide positions is between −10 and +8. In some embodiments, the range of nucleotide positions is between −7 and −4.

BRIEF DESCRIPTION OF THE DRAWINGS

FIG. 3A-FIG. 3C illustrates sample data generated using nucleic acid constructs of the present invention. FIG. 3A illustrates distribution of deletion lengths for deletions overlapping the expected cut site. FIG. 3B shows the fraction of reads showing each base being deleted. FIG. 3C shows a visualization of the underlying reads supporting the top and middle panels.

FIG. 4A-FIG. 4C illustrates a comparison of the data described in FIG. 3 and published data (Caribou) for the same gRNA targeting the endogenous locus.

FIG. 14 illustrates CRISPR-SENSR™ data to determine the tolerance of the system to mismatches at the −1, −3, and −4 positions in the gRNA. The gRNA targeting region is highlighted in light grey, and the predicted cut site is highlighted in darker grey. H=Not G (A, T, or C) according to IUPAC nucleotide codes.

DETAILED DESCRIPTION OF THE INVENTION

Figure 1:
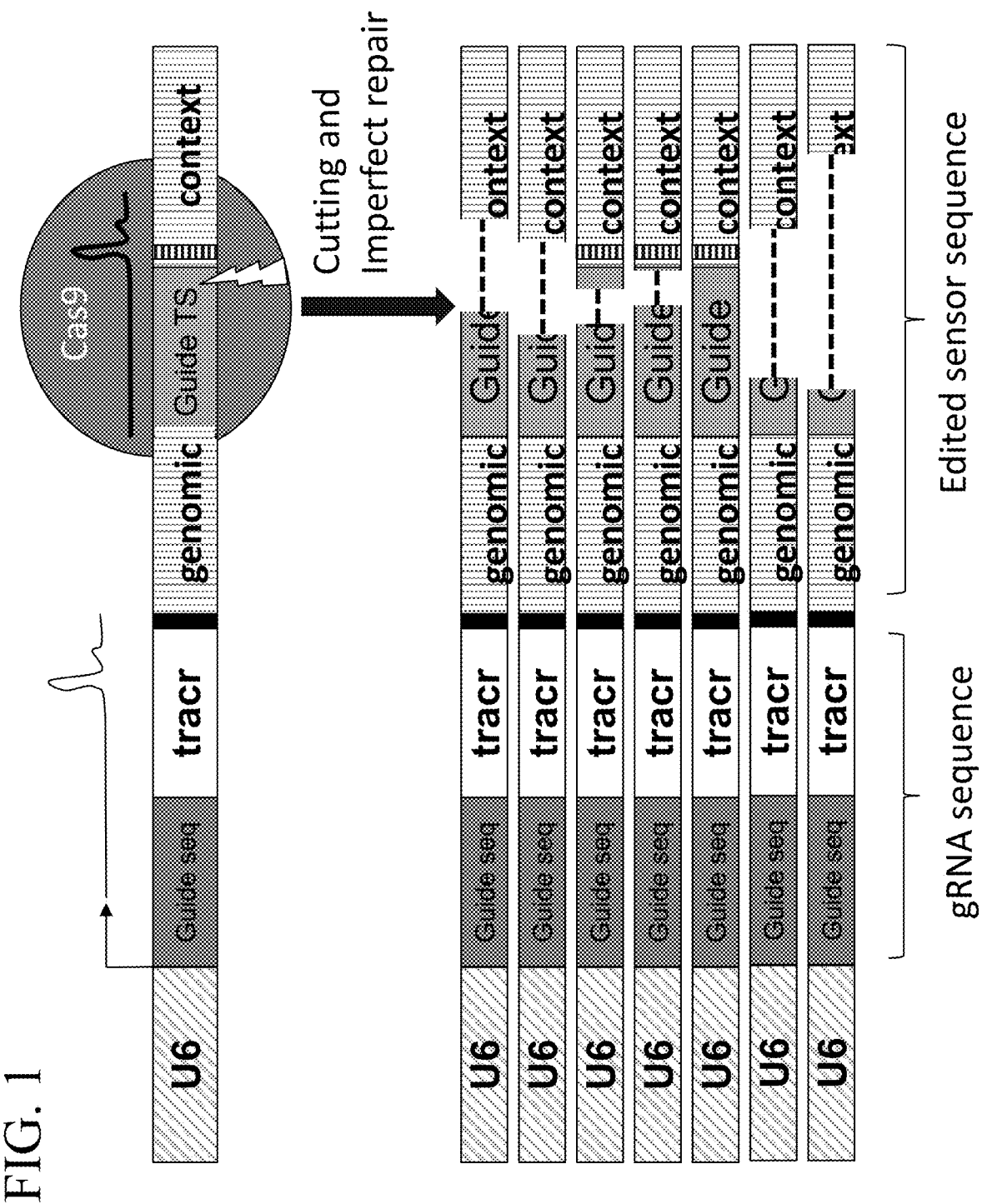
FIG. 1 illustrates a schematic of an exemplary sensor nucleic acid construct of the present invention and potential outcomes as a result of expression of the constructs in Cas9-expressing cells. gRNA sequences may comprise a dual-gRNA molecule or an sgRNA. Sensor sequences comprise a gRNA target sequence (light grey) and a PAM sequence (horizontal lines), and may further comprise the surrounding genomic context of the gRNA target sequence (vertical lines).
Figure 2:
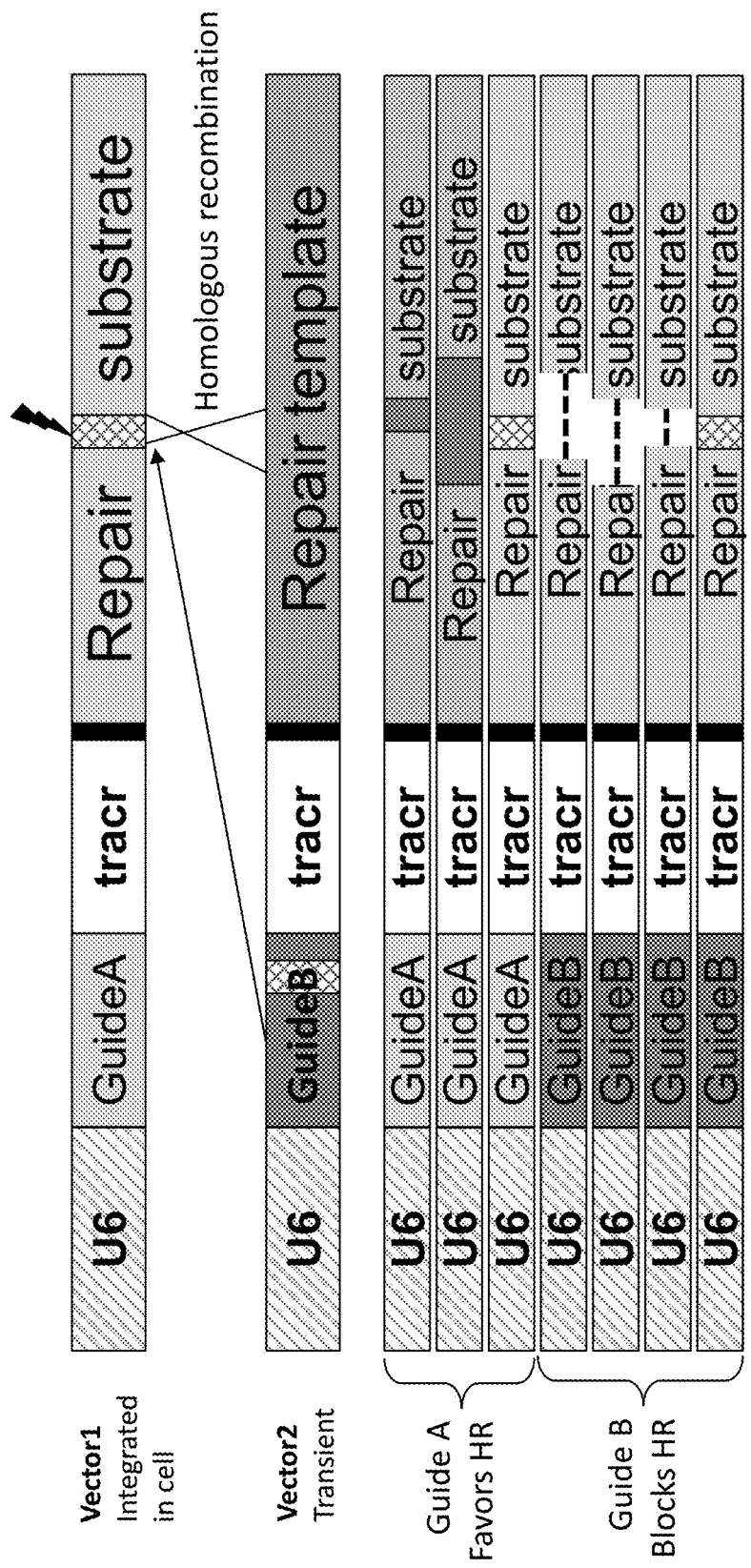
FIG. 2 illustrates a schematic of a homology-directed repair screening strategy using nucleic acid constructs of the present invention.

Prior to the present invention, the process of selecting optimal guide RNAs (gRNAs) for CRISPR/Cas9-mediated gene editing was limited to the use of predictive algorithms and cumbersome analysis of the resultant DNA alterations via PCR and agarose gel electrophoresis. These techniques are unable to accurately and quickly predict, in high-throughput, which gRNAs will render the desired gene alteration and which ones will not, leading to increased reagent consumption, expense, and effort in research utilizing the CRISPR/Cas9 system for genome editing. The current invention solves these problems and provides methods that enable high-throughput determination of effective gRNAs and generation of pre-designed gRNA libraries able to render specific and predictable DNA alterations.

Overview

In some embodiments, the specific alterations in a DNA sequence rendered by a particular gRNA are determined by expressing a nucleic acid construct comprising a first polynucleotide sequence encoding a gRNA and a second polynucleotide sequence comprising a corresponding target sequence in cells engineered to express a Cas9 endonuclease. Analysis of the resultant CRISPR/Cas9-mediated genetic alterations in the target sequence allows for the identification not only of effective gRNAs (i.e., gRNAs that result in the desired overall effect on gene expression, such as increased or decreased transcription), but also for the identification of gRNAs that mediate a particular genetic alteration (e.g. frameshift mutations, particular insertions, the nature of the DNA breaks, insertion of a repair template, and/or increased transcription of the target sequence). These techniques allow for the development and production of optimized gRNA libraries for use in genome engineering.

In some embodiments, the present invention provides methods of predicting the performance of a gRNA in an experimental system, wherein the gRNA has not been previously tested in the experimental system (e.g., an un-tested gRNA). In such embodiments, the model may predict the ability of the un-tested gRNA to mediate a desired effect on the target DNA sequence, such as a particular genetic alteration (e.g. frameshift mutations, particular insertions, the nature of the DNA breaks, insertion of a repair template) and/or alterations in the transcription of the target sequence. Such methods can thereby reduce the number of guides/gene required in future studies by allowing one of skill in the art to identify optimized gRNAs from a pool of untested gRNAs that are likely to mediate on-target genetic effects.

In some embodiments, the present invention provides methods for determining which gRNAs that have been previously used in an experimental system, such as a sub-genome wide or genome wide CRISPR/Cas9 screen, should be carried forward in the downstream analyses of the genetic screen data. Such methods thereby enable one of skill in the art to eliminate gRNAs that mediate off-target effects from downstream analyses, thereby decreasing the variability of the data and the likelihood of false-positive or false-negative results.

Definitions

As used herein, the use of the word "a" or "an" when used in conjunction with the term "comprising" in the claims and/or the specification may mean "one," but is also consistent with the meaning of "one or more," "at least one," and "one or more than one."

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein, a "cell" or "population of cells" refers to any type of cell suitable for use with the chosen transduction method, e.g., lentiviral transduction assays or electroporation. In general, the cells may be any cell type including immune cells (e.g., T cells, B cells, NK cells, NKT cells, macrophages, dendritic cells, monocytes, basophils, and neutrophils) structural cells (e.g., fibroblasts and epithelial cells), progenitor cells (e.g., thymocytes, megakaryocytes, and myeloblasts), stem cells (including hematopoietic stem cells, totipotent stem cells, pluripotent stem cells, and multipotent stem cells), and cells associated with a particular organ or organ system (e.g., brain cells and cells of the central nervous system, including neurons, ganglia, astrocytes, etc., gastrointestinal cells, lung cells, cardiac cells, liver cells, kidney cells, pancreatic cells, etc.) This includes cell lines and primary cells. Cell lines suitable for use with the present invention include 293T cells, THP1 cells, or fibroblast cell lines. Primary cells suitable for use with the present invention may be derived from human or non-human mammals, such as mice, rats, hamsters, guinea pigs, and other mammals commonly used in the art for research purposes. In some embodiments, the primary cells are primary immune cells such as T cells, B cells, peripheral blood mononuclear cells (PBMC), macrophages, and dendritic cells that have been obtained directly from a subject. In some embodiments, primary cells include cells that have been obtained from a subject than then cultured ex vivo to expand and/or differentiate the cells, such as bone marrow-derived cells or PBMCs.

As used herein, a "sensor construct" refers to a nucleic acid construct comprising, at a minimum, a first nucleic acid sequence encoding a gRNA and a second nucleic acid sequence comprising a corresponding gRNA target sequence. Sensor constructs may also be referred to as "CRISPR-SENSR™ constructs." In the context of a sensor construct, the first nucleic acid sequence encoding a gRNA is referred to herein as a "gRNA sequence" and the second nucleic acid sequence comprising a corresponding gRNA target sequence is referred to as a "sensor sequence" or a "SENSR™ sequence." In certain embodiments, the gRNA sequence encodes two separate RNA molecules that associate to form a functional gRNA complex. In such embodiments, the gRNA sequence encodes a crRNA which contains the RNA sequence that recognizes the target gRNA sequence in both the sensor sequence and the target genomic region of the host DNA, and a tracrRNA, which binds to the Cas9 protein. Association of the crRNA and tracrRNA forms an active gRNA complex, referred to herein as a "dual-gRNA." In certain embodiments, the portion of the crRNA that binds to the tracrRNA to form an active complex is a hairpin structure. In some embodiments, the gRNA sequence encodes a single RNA molecule that comprises both the crRNA sequence and the tracrRNA sequence. Such single-RNA molecule gRNAs are referred to herein as "single guide RNAs" or "sgRNAs." A collection of a plurality of heterogeneous sensor constructs is referred to herein as a "sensor construct library" or a "CRISPR-SENSR™ library."

As used herein, the terms "CRISPR-sensor system" and "CRISPR-SENSR™ system" are used interchangeably and refer compositions of sensor constructs and Cas 9 proteins utilized to identify gRNAs that result in a particular genetic alteration in a sensor sequence and/or an endogenous target sequence; gRNAs that result in changes in the transcription level of the sensor sequence and/or endogenous target sequence; and/or gRNAs that result in changes in the level of the protein encoded by the endogenous target sequence. gRNAs identified by a CRISPR-sensor system are referred to herein as "optimized gRNAs," and a collection of these optimized gRNAs is referred to herein as an "optimized gRNA library." One skilled in the art will appreciate that, while certain embodiments described herein are directed to use of the CRISPR-sensor system in the context of CRISPR/Cas9 methods of genome editing, this area is quickly developing, and this system can be adapted for use with any nucleic acid-guided/nucleic acid editing enzyme method. Other such methods include, but are not limited to, CRISPR/Cpf1 methods, single-stranded guide DNA (sDNA), and the *Natronobacterium gregoryi* Argonaute endonuclease methods.

CRISPR-Sensor Systems

In some embodiments, the present invention provides a CRISPR-sensor system comprising one or more sensor constructs (e.g., a sensor library) and a nucleic acid encoding a Cas9 protein. The CRISPR-sensor system as described herein can be applied to identify gRNAs that function efficiently in each of a variety of CRISPR/Cas9 systems, and to identify gRNAs that result in specific DNA alterations within each system. Screening of gRNAs with the CRISPR-sensor system enables the identification of gRNAs that result in specific deletions and/or insertions within the target sequence (e.g. predominant frame shifting insertions or deletions), and/or the identification of those gRNAs that result in a specific type of DNA break (e.g., blunt cuts or slight overhangs). Further, the CRISPR-sensor system allows for the determination of the size of insertion or deletion, and the identity of the inserted base pairs. As such, the CRISPR-sensor system identifies, in high-throughput, which gRNAs result in specific genetic alterations, and thus, which gRNAs will most effectively alter the sequence or expression of a given gene. Using the CRISPR-sensor system as described above, the skilled artisan can design optimized gRNA libraries using the most efficient gRNAs. These optimized gRNA libraries enable screening of more genes using the same number of cells and result in more robust signal-to-noise ratios thus enabling improved discovery of genes and agents that can provide therapeutic activities.

In some embodiments, a CRISPR-sensor system is introduced to a cell or population of cells. In some embodiments, the Cas9-encoding nucleic acid construct may be introduced to the cells prior to the introduction of the sensor construct or library. In some embodiments, the sensor construct or library may be introduced to the cells prior to the introduction of the Cas9-encoding nucleic acid construct. In some embodiments, the nucleic acid construct encoding the Cas9 protein and/or the sensor constructs are comprised in a viral vector. In such embodiments, the nucleic acid construct encoding the Cas9 protein and/or the sensor constructs are introduced by viral transduction. In some embodiments, the viral vector is a lentiviral vector. In some embodiments, the lentiviral vector is introduced at a titer of at least $1 \times 10^5$ infectious particles/mL. In some embodiments, the lentiviral vector is introduced at a titer between about $1 \times 10^5$ infectious particles/mL and $1 \times 10^{10}$ infectious particles/mL. In some embodiments, the lentiviral vector is introduced at a titer of about $1 \times 10^6$ infectious particles/mL. In some embodiments, the lentiviral vector is introduced at a titer of about $1 \times 10^7$ infectious particles/mL. In some embodiments, the nucleic acid construct encoding the Cas9 protein is an mRNA construct. In such embodiments, the Cas9-encoding mRNA construct may be introduced by transfection or electroporation.

Each of the Cas9 enzyme and the sensor constructs may be inducibly expressed using regulatable gene elements such as an inducible promoter. Inducible systems that may be used in the present invention include, for example, inducible U6 promoters or H1 promoters that can be used for inducible guides (Zhang et al. 2007 RNA 13:1375-1383; Henriksen et al. 2007 Nucleic Acids Res. 35:e67); the tet on/off systems, using tetracycline or doxycycline-regulated Cas9 (Dow et al. 2015 Nature Biotechnology 33:390-394); and small-molecule triggered Cas9 (Davis et al. 2015 Nat. Chem. Biol. 11:316-318). In this manner, expression of the Cas9 protein and the sensor library can be coordinated in order to optimize the genome-wide or sub-genome wide CRISPR-sensor screen. Additionally, using an inducible CRISPR-sensor system allows for further investigation of temporal expression relationships between genes.

Sensor Constructs

In some embodiments, the methods of the present invention comprise introducing a plurality of sensor constructs (e.g., a sensor library) into a cell or population of cells. As described above, sensor constructs are nucleic acid constructs comprising, at a minimum, a first nucleic acid sequence encoding a gRNA and a second nucleic acid sequence comprising a corresponding target nucleic acid sequence (e.g., a gRNA sequence and a sensor sequence). In general, the sensor constructs described herein are DNA polynucleotides. In some embodiments, the sensor constructs further comprise a promoter upstream of the gRNA sequence and a termination sequence downstream of the gRNA sequence, such that expression of the gRNA encoded by the gRNA sequence is mediated by the transcription mechanisms endogenous to the cell. In some embodiments, the sensor constructs comprise a promoter sequence upstream of the gRNA sequence and a termination sequence downstream of the sensor sequence such that the entirety of the sensor construct is transcribed. In some embodiments, the promoter is a polymerase III (Pol III) promoter, such as the RNA Pol III U6 promoter. In some embodiments, the termination sequence is a Pol III termination sequence (e.g., a poly-T sequence). One of skill in the art will appreciate that the nature of the Pol III promoter may vary without substantially affecting the gRNA transcription. Further, while the U6 promoter is specifically exemplified, other promoters including inducible, constitutive, and/or tissue specific promoters may be used. Similarly, any termination sequence may be used.

In further embodiments, the sensor construct further comprises a nucleic acid sequence encoding a reporter protein (e.g., a reporter gene). One of skill in the art will recognize that the order in which the gRNA sequence, sensor sequence, and reporter gene sequence occur in the sensor construct is not critical, so long as the arrangement permits expression of the gRNA, sensor sequence, and reporter protein in a cell. For example, in some embodiments, the reporter gene may be positioned immediately downstream of the promoter sequence and upstream of the gRNA and sensor sequences (e.g., Promoter sequence-reporter gene sequence-gRNA sequence-sensor sequence). In some embodiments, the reporter gene may be positioned immediately downstream of the gRNA and upstream of the sensor sequence (e.g., Promoter sequence-gRNA sequence-reporter gene sequence-sensor sequence). In some embodiments, the reporter gene may be positioned downstream of the gRNA and sensor sequence (e.g., Promoter sequence-gRNA sequence-sensor sequence-reporter gene sequence). Candidate reporter genes include, but are not limited to, lacZ (encoding B-galactosidase), gfp (encoding green fluorescent protein) or rfp (encoding red fluorescent protein). In some embodiments, the reporter gene may be used to identify cells that have been successfully transduced with the sensorconstructs. In some embodiments, notably in instances where the reporter gene is downstream of the sensor sequence, the effects of a particular gRNA on the sensor sequence may be assayed by a reporter assay in addition to sequencing of the sensor constructs.

Barcodes

In some embodiments, the sensor construct further comprises one or more nucleic acid tags located upstream and/or downstream from the sensor sequence. Herein, the terms "nucleic acid tag" and "barcode' are used interchangeably and refer to a short nucleotide sequence that provides information related to one or more aspects of a particular sensor construct (e.g., identifying unique sensor constructs, identifying a gRNA sequence comprised in a sensor construct, and/or identifying the sample source of the sensor construct). In some embodiments, the barcodes described herein comprise between 2 and 20 nucleotides. For example, a barcode may comprise 2, 3, 4, 5, 6, 7, 8, 9, 10, 11, 12, 13, 14, 15, 16, 17, 18, 19, or 20 nucleotides. In some embodiments, the barcodes are randomly generated. The barcodes described herein may be semi-unique barcodes or unique barcodes.

In some embodiments, the sensor construct comprises a semi-unique barcode. Herein, a semi-unique barcode is a barcode that is present on a subset of the sensor constructs comprised within a sensor library. Such barcodes are "semi-unique" in that they are unique to a particular subset of constructs but are present in more than one individual sensor construct in the total library. In some embodiments, a semi-unique barcode identifies a particular gRNA sequence and is referred to as a "gRNA barcode" or a "gRNA tag." In such embodiments, a gRNA barcode is present in a subset of constructs in the library, wherein each of the constructs in the subset comprises the gRNA sequence associated with the gRNA barcode. gRNA barcodes are "semi-unique" in that they are unique to a particular gRNA sequence and are therefore unique to a particular subset of constructs but are present in each construct comprised within that particular subset (i.e. present in more than one sensor construct in the total library). Typically, the semi-unique, gRNA barcode comprises fewer nucleotides than the gRNA sequence itself. In this manner, use of the semi-unique gRNA barcodes not only identifies which gRNA sequence is comprised within in a particular sensor construct, but also reduces the size of the amplicon required for sequencing.

In some embodiments, a semi-unique barcode identifies the sample from which a particular sensor construct is derived and are referred to herein as "sample barcodes" or "sample tags." For example, in some embodiments the sensor system may be used across multiple samples in a single experiment, wherein a sensor library is introduced separately into each sample. In such embodiments, the constructs in a sensor library that are introduced into a first sample may each be labeled with a first sample barcode, and the constructs in a sensor library that are introduced into a second sample may each be labeled with a second sample barcode. In this illustrative embodiment, the first and second samples barcodes are different from one another such that a sequencing read of a sensor construct derived from the first sample can be distinguished from a sequencing read derived from the second sample. In this manner, sample barcodes not only identify the sample source of a particular sequence read of a sensor construct but also allow for sample multiplexing.

In some embodiments, the sensor may comprise a unique barcode. In some embodiments, the unique barcode is a randomly generated nucleic acid sequence that is added to each sensor construct in a sensor library. This type of barcode enables the identification of unique cuts and aids in identifying unique sequence reads. The sequence information derived from the unique barcodes allows one of skill in the art to determine whether sequence reads from identically edited sensor sequences originated from the same genome edit (e.g., where the sensor DNA molecule was amplified by PCR to produce multiple copies of the edited sequence, or where an original cell comprising an edited sensor grew into multiple cells that were then sampled) or originated from two or more unique edits occurring in separate cells that produced the same edit pattern. Such barcodes are "unique" in that no two sensor constructs in a given experimental set-up will comprise the same unique barcode. In some embodiments, the sensor constructs may comprise one barcode (e.g. a semi-unique barcode or a unique barcode). In some embodiments, the sensor constructs may comprise two barcodes (e.g. one semi-unique barcode that identifies the gRNA and one unique barcode that identifies the particular copy of the sensor construct and thus identifies the origin of the genome edit). In some embodiments, the sensor constructs may comprise three or more barcodes (e.g. one semi-unique barcode that identifies the gRNA and two or more unique barcodes). In some embodiments, the sensor construct further comprises a universal primer site such that amplification of all sensor constructs may be done with a single pair of primers. Alternatively, template-specific primers may be used.

Sensor Sequences

In some embodiments, the nucleic acid constructs of the present invention comprise a first polynucleotide sequence encoding a gRNA and a second polynucleotide sequence comprising a corresponding gRNA target sequence. The polynucleotide sequences comprising the corresponding gRNA target sequence are referred to herein as "sensor sequences." Herein, a "gRNA target sequence" refers to a nucleic acid sequence approximately 20 base pairs in length recognized by and capable of binding to a gRNA. In some embodiments, the sensor sequence comprises the approximately 20 base pair gRNA target sequence in the context of the upstream and/or downstream endogenous genomic sequence (also referred to as the genomic context. See e.g., FIG. 1). In some embodiments, the sensor sequence may comprise the approximately 20 base pair gRNA target sequence in the context of a genomic sequence of an unrelated target gene (e.g. a gRNA target sequence in the incorrect genomic context). In such embodiments, the sensor sequence comprises a nucleotide sequence that is approximately 20 base pairs in length. In some embodiments, the sensor sequence comprises a nucleic acid sequence that is 25, 30, 40, 50, 60, 70, 80, 90, 100, 150, 200, 250, 500, 1000 or more nucleotides in length. In general, the sensor sequence comprises a protospacer adjacent motif (PAM) sequence. The PAM sequence is a short (2-6 base pair) sequence that is required for Cas9-mediated DNA cutting. Different PAM sequences have been identified in the context of different Cas9 enzymes (e.g. the PAM sequence for spCas9 is 5'-NGG-3' and the PAM sequence for saCas9 is 5'-NNGRRT-3'). As such, in some embodiments, the sensor sequence comprises a PAM sequence for spCas9 or saCas9.

Sensor Libraries

The terms "sensor construct library" or "CRISPR-SENSR™ library" as used herein refer to a collection of a plurality of sensor constructs. In some embodiments, the sensor construct library is genome-wide. As used herein, a "genome-wide sensor construct library" refers to a sensor construct library constructed to target genomic elements across substantially all of the genome. In some embodiments, the sensor construct library is subgenome-wide. As used herein a "subgenome-wide sensor construct library" refers to a sensor construct library that is constructed to target a subset of genomic elements (e.g., less than the entire genome). In some embodiments, a sensor construct library may comprise sensor constructs encoding gRNA targeting approximately 2000, 3000, 4000, 5000, 6000, or more genes. In general, a sensor construct library (either genome-wide or subgenome-scale) comprises multiple sensor constructs encoding different gRNAs that target the same genetic locus. For example, a sensor construct library may comprise 2, 3, 4, 5, 6, 7, 8, 9, 10, 11, 12, 13, 14, 15, or more different sensor construct constructs per gene, each encoding a different gRNA sequence targeting the same individual gene.

In some embodiments, a subgenome-wide sensor construct library comprises sensor constructs encoding gRNAs targeted to genes that are associated with a given disease or disorder such as an inflammatory disease, an autoimmune disease, asthma, and/or cancer. In some embodiments, the targeted genes are cell surface receptors. In some embodiments, the targeted genes are genes that have been identified using drug-combination and/or small molecule studies. In some embodiments, the targeted genes have an FDA-approved drug that is approved for the treatment of a particular disease(s) or disorder(s). In some embodiments, the targeted genes have a commercially available activator and/or inhibitor. In such embodiments, the nature of the drug (e.g., small molecule inhibitor, antibody, siRNA) is not critical so long as the drug is able to affect the function of the encoded protein product. As such, drugs that target either the gene expression or protein expression of a given target gene are contemplated. In some embodiments, the targeted genes do not have a currently available drug but are considered druggable. As used herein, "druggable" refers to any target gene or encoded protein for which a drug can be developed.

The present invention may use genome-wide or subgenome-wide sensor construct libraries for in vitro and/or in vivo screens. For in vivo screens, it is generally preferred to use a subgenome-wide sensor construct library. In some embodiments, sensor construct libraries may first be screened in vitro to determine gRNAs that result in the desired pattern of genetic alterations, thereby identifying optimal gRNAs for each gene and generating an optimized gRNA library. In such embodiments, the resulting optimized gRNA is smaller than the corresponding non-optimized gRNA library. For example, a sensor construct library may be generated wherein 10 sensor constructs are generated for each gene in the genome (e.g., 10 sensor constructs are generated for each target genomic sequence, wherein each of the 10 sensor constructs encodes a unique gRNA). Preliminary in vitro sensor screens may then identify 2 optimal gRNAs per gene. In this illustrative embodiment, the resulting optimized gRNA library is smaller than the corresponding non-optimized gRNA library (e.g., comprises 2 gRNAs/gene rather than 10 gRNAs/gene) but still targets the same number of genes as the non-optimized gRNA library (e.g., the optimized gRNA library and non-optimized gRNA library are both genome wide). Similar embodiments are contemplated for sub-genome wide optimized gRNA libraries, wherein the non-optimized sub-genome wide gRNA library comprises a number of gRNAs/gene that is greater than the number of gRNAs/gene in the optimized sub-genome wide library but the overall number of targeted genes is the same between the two libraries.

In some embodiments, the optimized gRNA libraries identified in an in vitro screen and can then be confirmed in an in vivo screen by introducing sensor constructs comprising the optimized gRNA library into an in vivo system.

Cas9

In some embodiments, sensor constructs described herein are introduced to a cell or population of cells that have been engineered to express a Cas9 protein. In some embodiments, the cells are engineered to express Cas9 by introducing a nucleic acid construct encoding the Cas9 protein (e.g., a DNA or mRNA nucleic acid construct). In some embodiments, the Cas9 protein is derived from *Streptococcus pyogenes* (SpCas9). In some embodiments, the Cas9 protein is derived from other bacteria strains including *Staphylococcus aureus* (SaCas9).

In some embodiments, the Cas9 protein is a wildtype (WT) Cas9 protein comprising two catalytically active domains (HNH and RuvC). gRNA-mediated binding of WT Cas9 to DNA results in double-stranded DNA breaks that are repair by non-homologous end joining (NHEJ) or homology-directed repair (HDR). In some embodiments, Cas9 is fused to proteins that recruit DNA-damage signaling proteins, exonucleases, or phosphatases to further increase the likelihood of alteration to the target sequence or the rate of repair of the target sequence.

In some embodiments, the Cas9 protein is a mutant version of Cas9, wherein one or both of the Cas9 catalytic domains have been altered to reduce the enzymatic activity of the Cas9 protein. In some embodiments, the mutant Cas9 protein is a Cas9 nickase mutant, wherein one or the other of the HNH or RuvC domains has been inactivated. The Cas9 nickase mutants retain DNA binding based on gRNA specificity, but are only capable of cutting one strand of DNA, resulting in a single-stranded break (i.e., a "nick"). In some embodiments, two complementary Cas9 nickase mutants (e.g. one Cas9 nickase mutant with an inactivated RuvC domain, and one Cas9 nickase mutant with an inactivated HNH domain) are expressed in the same cell with at least two sensor constructs. In such an embodiment each sensor construct encodes a gRNA corresponding to one of two respective target sequences; one target sequence on the sense DNA strand, and one on the antisense DNA strand. This dual-nickase system results in staggered double stranded breaks and can increase on-target specificity of the desired genetic alteration, as it is unlikely that two off-target nicks will be generated close enough to generate a double stranded break. In some embodiments, a Cas9 nickase mutant is co-expressed with a nucleic acid repair template to facilitate the incorporation of an exogenous nucleic acid sequence by homology-directed repair.

In some embodiments, the mutant Cas9 protein is a deactivated-Cas9 (dCas9) mutant, wherein both of the enzymatic domains of the Cas9 protein are engineered to be catalytically inactive. In some embodiments, dCas9 is fused to a heterologous protein that alters expression of a target gene or induces mutations in the target sequence. In some embodiments, dCas9 is fused to a transcriptional repressor, such as MAX-interacting protein 1. (MX11), Krüppel-associated box (KRAB) domain, or four concatenated mSin3 domains (SID4X). In particular embodiments, the transcriptional repressor is a KRAB domain. In some embodiments, dCas9 is fused to a transcriptional activator such as one or multiple repeats of the herpes simplex VP16 activation domain (e.g., VP64 or VP160) or the nuclear factor-κB (NF-κB) transactivating subunit activation domain (p65AD).

Sensor Library Screens

In some embodiments, the CRISPR-sensor system can be used to screen for gRNAs that function efficiently in each of a variety of CRISPR/Cas9 systems, and to identify gRNAs that result in specific DNA alterations within each system. The general experimental schematic of a CRISPR-screen screen is the introduction (e.g., by viral transduction) of an antibiotic resistance cassette together with a genome-wide or subgenome-wide library of sensor constructs to a cell line engineered to express Cas9 in vitro. Successfully transduced cells are identified by antibiotic selection and comprise at least one sensor construct. In some embodiments, the cells containing the sensor constructs and also expressing the Cas9 protein can be subjected to an environmental stimulus or, in screens assessing genes required for survival, cultured for a period of at least 7 days.

In some embodiments, the sensor screens are performed using the CRISPR interference (CRISPRi) systems (Gilbert et al. 2014 Cell 159:647), and the catalytically inactive dCas9. In some embodiments, dCas9 is fused to a transcriptional repressor such as, for example, 1\4AX-interacting protein 1 (MX11), Krüppel-associated box (DRAB) domain, or four concatenated mSin3 domains (SID4X). In certain embodiments, the transcriptional repressor is a KRAB domain. In such embodiments, the CRISPRi system represses transcription of genes rather than resulting in loss-of-function through DNA cutting. In some embodiments, dCas9 is fused to a heterologous enzyme, such as a cytidine deaminase, to introduce DNA mutations by DNA hypermutation.

In some embodiments, sensor screens are used with the CRISPR activation (CRISPRa) system. The CRISPRa systems also uses the dCas9 mutant, but results in gene activation rather than suppression. A variety of potential activator systems are known in the art, including but not limited to dCas9-Sun together with one or more transcription activator domains, including, for example one or multiple repeats of the herpes simplex VP16 activation domain (VP64 or VP160) or the nuclear factor-κB (NF-κB) transactivating subunit activation domain (p65AD). In certain embodiments, the CRISPRa Cas9 system is selected from the group consisting of single chain-VP64 fusion proteins (Gilbert et al. 2014 Cell 159:647), dCas9-VPR (Chavez et al. 2016 Nat Methods10.1038/nmeth.3312), or the SAM system (Konermann et al. 2015 Nature 517:583). (See also, Dominguez et al. 2016 Nat. Rev. Mol. Cell Biol. 17:5-15).

In some embodiments, sensor screens are performed using the Cas9 nickase mutants. In some embodiments, two complementary Cas9 nickase mutants (e.g. one Cas9 nickase mutant with and inactivated RuvC domain, and one Cas9 nickase mutant with an inactivated HNH domain) are expressed in the same cell with two gRNAs corresponding to two respective target sequences; one target sequence on the sense DNA strand, and one on the antisense DNA strand. This dual-nickase system results in staggered double-stranded breaks and can increase target specificity, as it is unlikely that two off-target nicks will be generated close enough to generate a double stranded break. In some embodiments, a Cas9 nickase mutant is co-expressed with a nucleic acid repair template to facilitate the incorporation of an exogenous nucleic acid sequence by homology-directed repair.

The CRISPR-sensor system as described herein can be applied in any of the above described methods of CRISPR/Cas9 utilization to identify gRNAs that function efficiently in each system, and to identify gRNAs that result in specific DNA alterations within each system. By way of example, the CRISPR-sensor system can be used in the context of a CRISPR/Cas9 screen in which the Cas9 enzyme comprises a wild type Cas9 (e.g., Cas9 in which both catalytic domains are active). Screening of gRNAs with the CRISPR-sensor system in this context would allow for the identification of those gRNAs that result in specific deletions and/or insertions within the target sequence (e.g. predominant frame shifting insertions or deletions), and/or the identification of those gRNAs that result in a specific type of double-stranded DNA breaks (e.g., blunt cuts or slight overhangs). Further, the CRISPR-sensor system allows for the determination of the size of insertion or deletion, and the identity of the inserted base pairs. As such, the CRISPR-sensor system identifies, in high-throughput, which gRNAs result in specific gene alterations, and thus, which gRNAs will be the most effectively alter the sequence or expression of a gene in the context of a CRISPR/Cas9 screen in which the Cas9 enzyme comprises a wild type Cas9.

By way of additional example, the CRISPR-sensor system can be used in the context of a CRISPR/Cas9 screen in which the Cas9 enzyme comprises a dCas9 mutant (e.g., Cas9 in which both catalytic domains are inactive) fused with a transcriptional repressor protein (such as a KRAB-containing repressor protein) (e.g. a CRISPRi system). Screening of gRNAs with the CRISPR-sensor system in this context would allow for the identification of those gRNAs that resulted in reduction in transcription of the endogenous target sequence through quantification of mRNA transcription (e.g., qPCR) or expression of the encoded protein product (e.g., using flow cytometry or ELISA). As such, the CRISPR-sensor system identifies, in high-throughput, which gRNAs result in specific alterations in gene expression, and thus which gRNAs will be the most effectively alter or repress the expression of a target gene. Similar assay readouts could be performed for a CRISPR/Cas9 screen in which the dCas9 enzyme is fused to a transcriptional activator (e.g. a CRISPRa system). In this aspect, the CRISPR-sensor system would identify those gRNAs that resulted in increased gene transcription and/or protein expression.

CRISPR-Sensor System: Methods of Use

Variations of methods of using the CRISPR-sensor system are described herein, but generally comprise introducing a CRISPR-sensor library into a population of cells engineered to expressed Cas9 or a mutant version of Cas9. This population of cells is cultured to allow expression of the gRNAs contained in the sensor constructs and the Cas9 protein, resulting in gRNA binding and directing of Cas9 to the corresponding target sequence present in both the sensor construct (e.g., present in the sensor sequence) and the endogenous DNA sequence. The effects of a particular gRNA/Cas9 combination can be determined through sequencing methods known in the art (e.g. Next-Generation sequencing, NGS), quantitative methods of determining changes in gene transcription (e.g. quantitative PCR (qPCR)), or quantitative methods of protein expression (e.g. ELISA or flow cytometry).

For example, in some embodiments, cells are modified to express a Cas9 protein with two catalytically active domains (e.g. WT Cas9) and a genome-wide or subgenome-wide sensor library is introduced into the Cas9-modified cells. In this aspect of the invention, binding of the gRNA/Cas9 complex to the sensor and/or endogenous DNA sequence results in Cas9-induced double stranded breaks (DSB) which are then repaired by endogenous DNA repair mechanisms (e.g. non-homologous end joining). In some embodiments, these repair mechanisms result in gene alterations such as insertions, deletions, and/or mutations that can result in altered gene expression. Amplification and sequencing of the sensor construct allows for the correlation of gRNA expression with a particular gene alteration, as the altered sensor sequence and the gRNA are present in the same amplicon. A pattern of alterations in the sensor sequence can be determined for each construct in the library, and optimized gRNAs selected based on their ability to result in a desired pattern of alterations.

In some embodiments of the invention, a pattern of alterations in the sensor sequence and/or the endogenous target DNA sequence is determined. As used herein, a "pattern of alterations" encompasses sequence and/or epigenetic alterations in the sensor sequence and/or the endogenous target DNA sequence. In some embodiments, these alterations are a result of endogenous DNA repair mechanisms, such as non-homologous end joining (NHEJ) or homology-directed repair (HDR). In some embodiments, these alterations are a result of the actions of heterologous proteins fused to the Cas9 protein, such as cytidine deaminase. These alterations can include, but are not limited to, changes in the total number of base pairs comprised in a given target sequence (e.g. through insertions or deletions of any size), alterations in the identity of one or more base pairs (e.g. mutations or substitutions, including synonymous and nonsynonymous substitutions, transversions, transitions, missense mutations, nonsense mutations, and/or frameshift mutations), incorporation of a repair template (e.g., repair mediated by homology-directed repair), and/or alterations in epigenetic DNA modifications (e.g. methylation status or histone modifications such as acetylation, methylation, and/or phosphorylation status). In some embodiments, a pattern of alterations refers to the presence or absence of evidence of DNA cutting (e.g., the presence or absence of insertions, deletions, and/or mutations).

In some embodiments, patterns of alterations are identified through sequencing of a plurality of sensor amplicons. In some embodiments, a "plurality of sensor amplicons" refers to a population of heterogeneous sensor amplicons (e.g., amplicons of sensor constructs that comprise different gRNA sequences and sensor sequences). In some embodiments, the amplicons are sequenced by Next-Generation sequencing. In some aspects of this invention, the amplicons are sequenced by paired-end sequencing. In some aspects of this invention, the amplicons are sequenced by bisulfite sequencing to detect alterations in the methylation patterns in the sensor amplicon. In some aspects of the present invention, the amplicons are sequenced by high-throughput sequencing. In some aspects of the present invention, the sequencing is performed at an average sequencing depth of at least 50 reads/amplicon. In some aspects, the sequencing is performed at an average sequencing depth of between about 50 reads/amplicon to about 250 reads/amplicon. In some embodiments, the sequencing is performed at an average sequencing depth of at least 75, 100, 125, 150, or 200 reads/amplicon. In some embodiments, the sequencing is performed at an average sequencing depth of 150 reads/amplicon.

In some embodiments, a pattern of transcriptional changes in an endogenous target sequence and/or sensor sequences is determined. As used herein a "pattern of transcriptional changes" refers to changes or alterations in the transcript levels of the endogenous target sequence and/or sensor sequences in cells comprising a sensor construct compared to a population of control cells. As used herein, "control cells" refer to cells in which the endogenous target sequence or the sensor sequence is unaltered. In some embodiments, a control cell may refer to a population of cells that does not comprise a sensor construct. In some embodiments, a control cell may refer to a population of cells that comprises a sensor construct wherein the gRNA sequence of the construct does not result in direction of Cas9 to a target sequence in either the sensor sequence or the endogenous genomic sequence (e.g. a non-targeting gRNA sequence). In some embodiments, changes or alterations in the transcript levels refers to increased or decreased levels of mRNA transcripts of the endogenous target sequence. In some embodiments, "increased transcription" refers to an increase in the level of mRNA transcripts for a particular gene compared to the levels observed in a control cell. In some embodiments, increased transcription may refer to a 5%, 10%, 15%, 20%, 30%, 40%, 50%, 100%, 200%, 300%, 400%, 500%, 1000% or more increase in the mRNA transcripts of an endogenous target sequence compared to the levels of the same mRNA transcript observed in a control cell. In some embodiments, "decreased transcription" refers to a decrease in the level of mRNA transcripts for a particular gene compared to the levels observed in a control cell. In some embodiments, decreased transcription may refer to a 5%, 10%, 15%, 20%, 30%, 40%, 50%, 60%, 70%, 80%, 90% or 100% reduction in the mRNA transcripts of an endogenous target sequence compared to the levels of the same mRNA transcript observed in a control cell. Changes or alterations in the transcript levels may be determined by methods known in the art (e.g. qPCR, RNA-Seq, or microarrays). In some embodiments, changes or alterations in the transcript levels of the endogenous target sequence can be measured by assaying for the encoded protein product by methods known in the art (e.g. enzyme-linked immunosorbent assay (ELISA), Western blot, or flow cytometry). In some embodiments, a pattern of transcription changes is determined by qPCR analysis of the SENSR™ sequence.

As used herein a "desired pattern of alterations" and a "desired pattern of transcriptional changes" refer to a pattern of alterations or transcriptional changes, respectively, which is selected for based on a desired outcome in a particular CRISPR/Cas9 system. In some embodiments, the desired pattern of alterations and/or pattern of transcriptional changes is used to classify gRNAs into different groups based on their observed functionality. For example, gRNAs that demonstrate effective DNA cutting based on the observed pattern of alterations in the sensor sequence may be classified as "good" or "functional" gRNAs, while gRNAs that do not demonstrate effective DNA cutting based of a lack of observed pattern of alterations in the sensor sequence or demonstrate a pattern of alterations that is insufficient to result in the ultimate desired outcome (e.g., results in changes that are insufficient to inactivate a gene) may be classified as "bad" or "non-functional" gRNAs. These classifications may be confirmed by functional assays, such as assays assessing cell proliferation, cell viability, and/or response to an environmental stimulus, such as treatment with a drug.

The desired pattern of alterations and/or transcriptional changes for one desired outcome will likely be different than the desired pattern of alterations and/or transcriptional changes for an alternative desired outcome. By way of example, in instances where gene inactivation is desired, a desired pattern of alterations may comprise alterations such as missense mutations resulting in premature stop codons, deletion of a substantially large number of base pairs, or increased DNA methylation. In such instances, a desired pattern of transcriptional changes may comprise substantially reduced transcription of the endogenous target sequence and/or substantially reduced expression of the encoded protein. Alternatively, in instances where gene editing is desired (e.g. incorporation of an exogenous transgene), a desired pattern of alterations may comprise efficient and high-fidelity incorporation of a repair template. In such instances, a desired pattern of alterations and/or transcriptional changes may comprise increased transcription of the repair template sequence and/or increased expression of the encoded transgenic protein.

Optimized gRNAs and Optimized gRNA Libraries

In some embodiments, the pattern of sequence alterations identified through sequencing of a plurality of sensor amplicons is used to identify optimized gRNAs to produce optimized gRNA libraries. By way of example, a particular optimized gRNA may be selected based on the frequency of insertions, deletions (e.g., "indel" such as delG, or G→STOP) or missense mutations generated in the sensor sequence. An optimized gRNA library comprising such optimized gRNAs would, for example, greatly increase the probability of generating a non-functional gene product. In some embodiments, the ability of a gRNA to induce a similar pattern of alterations in the endogenous DNA sequence is confirmed by functional assays. In such embodiments, gRNAs that result in the desired pattern of alterations and demonstrate efficacy in the functional assays are identified as optimized gRNAs. In some embodiments, a pattern of transcriptional changes and a pattern of alterations are correlated with one another to identify optimized gRNAs that result in specific genetic alterations and specific transcriptional changes (e.g. a specific deletion identified by sequences of the sensor construct and/or the endogenous target sequence is correlated with decreased mRNA transcript levels determined by qPCR).

In some embodiments, a lack of alterations in the sensor sequence, indicates that the corresponding gRNA is a non-functional gRNA and should not be used in future screen. In some embodiments, the identification of a non-functional gRNA allows for that gRNA and any corresponding samples to be removed from downstream analyses of experiments, such as genetic screens, that have been previously performed. Elimination of non-function gRNAs from data analyses would improve the signal-to-noise ratio of such systems and allow for more precise identification of gene function or identification of genes of interest.

In some embodiments, the CRISPR-sensor system can be used to identify high-fidelity gRNAs. As used herein, "high-fidelity gRNAs" refer to gRNAs that only binds in instances where the actual target sequence is 100% identical to the proposed target sequence. For purposes of the present invention, the term "high-fidelity gRNA" also includes a guide with a 1 base pair point mutation that leads to significant off-target cutting, but that point mutation is not found in the natural genome (e.g., not even in as a rare polymorphism). Such gRNAs are thus highly sensitive to the presence of mutations and will not bind when the actual target sequence is not 100% identical to the proposed target sequence. In some embodiments, high-fidelity gRNAs are identified by generating multiple (e.g., at least 100, 110, 120, 130, 150, 200, 300, 400, or 500 or more) sensor constructs, each encoding unique gRNAs directed against a sensor sequence that is 100% identical to the proposed gRNA target sequence or against a sensor sequence that comprises a point mutation at at least one base pair. High-fidelity gRNAs may also be used to identify mutations in sequences immediately adjacent to the target sequence, such as the protospacer adjacent motif (PAM). High-fidelity gRNAs are identified as those that result in alterations of the sensor sequences with 100% identity to the proposed target sequence and do not result in alterations of the sensor sequences that comprise a point mutation in at least one base pair. These high-fidelity gRNAs can be used in the context of mutant-selective cutting (e.g.

to determine the presence or absence of at least one mutation in a given target sequence). In some embodiments, the high-fidelity gRNAs can be used to determine the presence or absence of a single-nucleotide polymorphism (SNP). In some embodiments, the target sequence is a known disease allele. In some aspects of this embodiment, the high-fidelity gRNAs can be used to target specific alleles that occur in a given disease.

Predicting gRNA Performance Using CRISPR-Sensor Systems

In some embodiments, the present invention provides methods of predicting the performance of a gRNA that has not been previously tested in an experimental system. In such embodiments, a screen is performed using the CRISPR-sensor system as described above. gRNAs that result in the desired pattern of genetic alterations (identified by sequencing of sensor constructs) and/or the desired pattern of transcriptional alterations are classified as "good" or "functional" gRNAs, while gRNAs that do not result in the desired pattern of genetic alterations and/or the desired pattern of transcriptional alterations are classified as "bad" or "non-functional" gRNAs. Multiple features of each group are then analyzed to develop a model that is capable of predicting the ability of a given gRNA to mediate the desired pattern of genetic alterations and/or desired pattern of transcriptional changes (i.e., capable of identifying a given gRNA as a "good" or a "bad" gRNA), even when that gRNA has not been previously tested in the particular experimental system of interest. A variety of features may be used in analyzing the characteristics of "good" and "bad" gRNAs. These features include, but are not limited to, the melting temperature of the gRNA, the GC content of the gRNA sequence, sequences of micro-homology (short stretches of identical nucleotides) present in the gRNA sequence, the type of nucleotide present at particular positons in the gRNA sequence (e.g., purine or pyrimidine), the identity of nucleotides present at particular positions in the gRNA sequence (e.g., A, T, C, G), and the location of the gRNA target site in the surrounding genomic context (e.g., a target site overlapping a splice site, a target site comprised within a coding region, or a target site overlapping a protein domain).

In some embodiments, the features described above are analyzed over the entirety of the gRNA sequence. In some embodiments, the features described above are analyzed over a portion of the gRNA sequence or at particular nucleotide positions in the gRNA sequence. Throughout the specification, the numbering of the positions in a gRNA is based on the 20 nucleotide sequence within the gRNA that mediates specific binding of the gRNA to the target DNA sequence, wherein the 5' terminal position is −20 (e.g., the "beginning of the gRNA") and wherein the 3' terminal position of this 20 nucleotide sequence is −1 (e.g., the "end of the gRNA"). The position immediately 3' to the end of the gRNA (i.e., position −1) is position 0, with the remaining nucleotides of the gRNA proceeding consecutively as +1, +2, +3, +4, +5, etc. Using this numbering system, the expected DNA cleavage site is between positions −4 and −3. In some embodiments, the features described above are analyzed between positions −10 to position −8 of the gRNA. In some embodiments, the features described about are analyzed between positions −7 to −4.

In some embodiments, the model described above is developed using a sensor library and is used to predict the gRNA performance of one or more, previously un-tested gRNAs that were not comprised in the sensor library used for model development. An "un-tested" gRNA refers to a gRNA that has not been previously used in a particular experimental system. In some embodiments, the gRNAs in the sensor library and the un-tested gRNAs target genomic sequences derived from the same species. For example, in some embodiments, the gRNAs used for model development and the untested gRNAs both target human genomic sequences or both target murine genomic sequences). In some embodiments, the gRNAs in the sensor library and the un-tested gRNAs target genomic sequences derived from different species. For example, in some embodiments, the gRNAs used for model development target human genomic sequences and the untested gRNAs target non-human genomic sequences. In some embodiments, the gRNAs used for model development target non-human genomic sequences and the untested gRNAs target human genomic sequences. In some embodiments, the non-human species is a mouse, rat, hamster, rabbit, or other mammal commonly used for research purposes.

In some embodiments, the model described above is developed using a sensor library and is used to analyze the gRNA performance of one or more gRNAs that were not comprised in the sensor library used for model development, but have been previously tested in a particular experimental system. In such embodiments, the methods described herein can identify which gRNAs and corresponding samples should be carried forward in downstream analyses of the genetic screen data. As an illustrative embodiment, a CRISPR/Cas9 screen may have been previously performed, wherein multiple gRNAs targeting each gene in the screen were used (e.g., 5 guides/gene, 10 guides/gene, etc.). In such experiments, not all of the guides will mediate alteration of the target sequence with the same efficiency or by the inducing the same genetic alteration. These differences in guide efficiency and mechanism introduce variability into the resulting sequencing data and can make results difficult to interpret. For example, in a screen using 10 gRNAs/gene, 5 of the gRNAs targeting a particular gene may result in cell death and the remaining 5 gRNAs may result in no effect on cell viability, making it difficult to draw a reasonable conclusion about the effect of that particular gene on cell viability. The methods and models described herein enable one of a skill in the art to identify which of these 10 gRNAs likely resulted in on-target effects (e.g., "good" gRNAs) and which gRNAs generated off-target effects (e.g., "bad" gRNAs), based on previous analysis of the performance of unrelated gRNAs.

EXAMPLES

Example 1: Generation of CRISPR-SENSR™ Library Lentivirus

To generate lentivirus containing a library of CRISPR-SENSRs™, 289×10$^6$ of LentiX-293 T cells were plated out in a 5-layer CellSTACK 24 hours prior to transfection. 18 mL of serum-free OptiMEM and 1212 μL of TransIT-293 were combined and incubated for 5 minutes before combining helper plasmids (58 μg VSVG and 115 μg PAX2-Gag-Pol) with 231 μg of plasmid encoding 60,000 CRISPR-SENSRs™ driven by a human U6 promoter, with puromycin and fluorescent protein markers. After 20 minutes, this mixture was added back to cells with fresh media. Media was replaced 18 hours after transduction, and virus was collected 48 hours post-transfection. After passing through a 0.45 μm filter, viral supernatant was aliquoted and stored at −80° C.

Example 2: Generation of Cas9 Expressing Lentivirus and Establishment of Cas9 Cell Lines The lentivirus construct used to generate Cas9-expressing T cells contains either the SFFV or the EF1a promoter expressing spCas9-T2A followed by a blasticidin or Thy1.1 selection cassette. To generate lentivirus containing Cas9, 289×10$^6$ of LentiX-293 T cells were plated out in a 5-layer CellSTACK 24 hours prior to transfection. 18 mL of serum-free OptiMEM and 1212 µL of TransIT-293 were combined and incubated for 5 minutes before combining helper plasmids (58 µg VSVG and 115 µg PAX2-Gag-Pol) with 231 µg of plasmid encoding Cas9 and either blasticidin or Thy1.1. After 20 minutes, this mixture was added back to cells with fresh media. Media was replaced 18 hours after transfection, and virus was collected 48 hours post-transfection. After passing through a 0.45 µm filter, the virus was concentrated with an Amicon spin filtration column so that final titer of infectious units was 10×10$^6$ infectious units per mL, as determined by function titration on HT1080 cells. Virus was aliquoted and stored at −80° C.

Cell lines were infected with Cas9-expressing lentivirus (pKSQ006) and selected with blasticidin S for at least one week. Expression of Cas9 protein was verified by immunofluorescence and flow cytometry with an anti-Cas9 antibody (Cell Signaling Technologies).

Example 3: CRISPR-SENSR™ Library Screen

Cell lines expressing Cas9 protein were first titrated with CRISPR-SENSR™ library virus. Cells were infected with varying doses of library lentivirus in 6-well dishes and selected with puromycin for three days. A level of infection was selected that resulted in 50% or less survival of cells at day 4 (multiplicity of infection <1). The volume of virus and number of cells were scaled up such that a number of cells approximately one thousand-fold times the size of the library were infected with the CRISPR-SENSR™ library lentivirus pool (i.e. 50 million infected cells for a library containing 50,000 CRISPR-SENSRs™). Puromycin was added 24 hours after virus addition and cells were selected in puromycin for three additional days. After puromycin selection, cells were split into new flasks, and a cell pellet was set aside for an early time point (4 days post infection). Infected cells were cultured continuously for 14 days post-lentiviral infection. Cells were split into new flasks when confluent, with cell pellets saved for genomic DNA preparation and sequencing at each time point.

Example 4: CRISPR-SENSR™ Library Sequencing

Genomic DNA was extracted from cell pellets of 100 million cells using a QIAmp genomic DNA blood kit (Qiagen). 100 mg of purified genomic DNA was PCR amplified using Taq DNA polymerase and primers binding the lentivirus upstream and downstream of the guide-tracr-SENSR™ sequence. Sequencing was performed on a NextSeq500 sequencing instrument (Illumina) with a 150-cycle paired-end DNA sequencing kit to read both the sequence of the guide and the SENSR™ sequence.

Example 5: CRISPR-SENSR™ System Screens

Proof of concept studies for the CRISPR-SENSR™ system were performed in the human colon cancer cell line, RKO, and the human fibrosarcoma cell line, HT1080. As shown in FIG. 3, expression of a nucleic acid construct expressing (i) a gRNA targeting ERBB2 (also known as HER2) and (ii) the corresponding ERBB2 target sequence in cells expressing (e.g., an ERBB2 CRISPR-SENSR™ construct) Cas9 resulted in a pattern of deletions in the ERBB2 target sequence. These data demonstrate the functionality of the CRISPR-SENSR™ system in two distinct human cell lines, as indicated by the distribution of deletion lengths for those deletions overlapping the expected cut site (FIG. 3A) and the fraction of reads where each base is deleted (FIG. 3B). This data is supported by visualization of the underlying reads (FIG. 3C). Herein, each row in FIG. 3 Corresponds to an individual sequencing read. Each base position was colored blue if the base was deleted in that read. The region shaded light grey represents the gRNA target site, and region shaded in darker grey represents the expected cut site (−3). The pattern of alterations (e.g., the pattern of deletions) was comparable to the pattern of alterations observed for cuts made in the endogenous genomic target sequence when utilizing the same gRNA (FIG. 4, See van Overbeek et al. (2016) *Molecular Cell*, 63:633-646, for comparison reference). Table 1 describes the reference sequence with the binding sequence for the gRNA denoted in bold and the expected cutting site denoted with an underline. Cas9-mediated edits of this reference sequence are described in Table 2. Therefore, the CRISPR-SENSR' system was able to effectively alter the SENSR' sequence such that a pattern of alterations (e.g. deletions) was detected. Further, CRISPR-SENSR' system was able to identify specific aspects of the alteration (e.g. length of deletion and the specific base pairs that are deleted).

TABLE 1

| Unedited Reference SENSR ™ Sequence | |
|---|---|
| Unedited Reference Sequence SEQ ID NO: 1 | AGCATAGCAAGTTTAAATAAGGCTAGTCCGT TATCAACTTGAAAA<u>A</u>GTGGCACCGAGTCGGT GCTTTTTTTGGAATAAAGATTGTGTGAGCAG CCTGCATTACCTACGATGGTAACCAAAGCTG ATTGACTGGGATGCTTT |

TABLE 2

Edited SENSR ™ Sequences

| SEQ ID NO: | Edited SENSR ™ Sequence | # of times observed |
|---|---|---|
| | Day14 | |
| 2 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TA-GATGGTAACCAAAGCTGATTGACTGGGATGCTTT | 52 |

TABLE 2-continued

Edited SENSR ™ Sequences

| SEQ ID NO: | Edited SENSR ™ Sequence | # of times observed |
|---|---|---|
| 3 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTG-------<br>--CGATGGTAACCAAAGCTGATTGACTGGGATGCTTT | 33 |
| 4 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCA-----<br>--------TAACCAAAGCTGATTGACTGGGATGCTTT | 27 |
| 5 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCATTACC<br>-ACGATGGTAACCAAAGCTGATTGACTGGGATGCTTT | 22 |
| 6 | AGCATAGCAAGTTTAAATAAGGCTAGTCCGTTATCAACTTGAAAAAGTGGCA<br>CCGAGTCGGTGCTTTTTTTGGAATAAAG-TTGTGT----------------<br>---GATGGTAACCAAAGCTGATTGACTGGGATGCTTT | 15 |
| 7 | AGCATAGCAAGTTTAAATAAGGCTAGTCCGTTAT---CTTGAAAAAGTGGCA<br>CCGAGTCGGTGCTTTTTTTGGAATAAAGATTGTGTGAGCAGCCTGCATTACC<br>TACGATGGTAACCAAAGCTGATTGACTGGGATGCTTT | 14 |
| 8 | AGCATAGCAAGTTTAAATAAGGCTAGTCCGTTATCAACTTGAAAAAGTGGCA<br>CCGAGTCGGTGCTTTTTTTGGAAT-AAGATTGTGTGAGCAGC---------<br>--CGATGGTAACCAAAGCTGATTGACTGGGATGCTTT | 14 |
| 9 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGC------<br>-------GTAACCAAAGCTGATTGACTGGGATGCTTT | 14 |
| 10 | AGCATAGCAAGTTTAAATAAGGCTAGTCCGTTATCAACTTGAAAAA-TGGCA<br>CCGAGTCGGTGCTTTTTTTGGAATAAAGATTGTGTGAGCAGCCTGCATTACC<br>TACGATGGTAACCAAAGCTGATTGACTGGGATGCTTT | 12 |
| 11 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCATTACC<br>TACGAT-GTAACCAAAGCTGATTGACTGGGATGCTTT | 11 |
| 12 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCATTACC<br>TACGATGGTAACCAAAGCTGATTGACTGGGATGCTTT | 10 |
| 13 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCATTACC<br>TACGATGGTAACCAAAGCTGATTGACTGGGATGCTTT | 10 |
| 14 | AGCATAGCAAGTTTAAATAAGGCTAGTCCGTTATCAACTTGAAAAAGTGGCA<br>CCGAGTCGGTGC-TTTTTTGGAATAAAGATTGTGTGAGCAGCCTGCATTACC<br>TACGATGGTAACCAAAGCTGATTGACTGGGATGCTTT | 7 |

Day 11

| 15 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCATTACC<br>TACGATGGTAACCAAAGCTGATTGACTGGGATGCTTT | 176 |
| 16 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCA-----<br>TAACCAAAGCTGATTGACTGGGATGCTTT | 30 |
| 17 | AGCATAGCAAGTTTAAATAAGGCTAGTCCGTTATCAACTTG--AAGTGGCAC<br>CGAGTCGGTGCTTTTTTTGGAATAAAGATTGTGTGAGCAGCCTGCATTACCT<br>ACGATGGTAACCAAAGCTGATTGACTGGGATGCTTT | 24 |
| 18 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCATTACC<br>TACGAT-GTAACCAAAGCTGATTGACTGGGATGCTTT | 22 |
| 19 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGCATTACC<br>TA-----GTAACCAAAGCTGATTGACTGGGATGCTTT | 22 |
| 20 | AGCATAGCAAGTTTAAATAAGGCTAGTCCGTTATCAACTTGAAAAAGTGGCA<br>CCGAGTCGGTGCTTTTTTTGGAATAAAGATTGTGTGAGCAGCCTGC------<br>-------GTAACCAAAGCTGATTGACTGGGATGCTTT | 19 |

TABLE 2-continued

Edited SENSR™ Sequences

| SEQ ID NO: | Edited SENSR™ Sequence | # of times observed |
|---|---|---|
| 21 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TACG--GGTAACCAAAGCTGATTGACTGGGATGCTTT | 16 |
| 22 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TAC-ATGGTAACCAAAGCTGATTGACTGGGATGCTTT | 16 |
| 23 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC -ACGATGGTAACCAAAGCTGATTGACTGGGATGCTTT | 16 |
| 24 | AGCATAGCAAGTTTAAATAAGGCTAGTCCGTTATCAACTTGAAAAAGTGGCA CCGAGTCGGTGCTTTTTTTGGAATAAAGA-TGTGTGAGCAGCCTGCATTACC TACGATGGTAACCAAAGCTGATTGACTGGGATGCTTT | 16 |
| 25 | AGCATAGCAAGTTTAAATAAGGCTAGTCCGTTATCAACTTGAAAAAGTGGCA CCGAGTCGGTGCTTTTTTTGGAATAAAG-TTGTGTGAGCAGCCTGCA-TACC TACGATGGTAACCAAAGCTGATTGACTGGGATGCTTT | 13 |
| 26 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TA-GATGGTAACCAAAGCTGATTGACTGGGATGCTTT | 10 |
| 27 | AGCATAGCAAGTTTAAATAAGGCTAGTCC-TTATCAACTTGAAAAAGTGGCA CCGAGTCGGTGCTTTTTTTGGAATAAAGATTGTGTGAGCAGCCTGCAT---- ----------ACCAAAGCTGATTGACTGGGATGCTTT | 9 |
| 28 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TA------TAACCAAAGCTGATTGACTGGGATGCTTT | 8 |
| 29 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTAC- -ACGATGGTAACCAAAGCTGATTGACTGGGATGCTTT | 7 |
| Day 8 | | |
| 30 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TACGATGGTAACCAAAGCTGATTGACTGGGATGCTTT | 43 |
| 31 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTG --CGATGGTAACCAAAGCTGATTGACTGGGATGCTTT | 23 |
| 32 | AGCATAGCAAGTTTAAATAAGGCTAG-CCGTTATCAACTTGAAAAAGTGGCA CCGAGTCGGTGCTTTTTTTGGAATAAAGATTGTGTGAGCAGCCTGCA-TACC TACGATGGTAACCAAAGCTGATTGACTGGGATGCTTT | 13 |
| 33 | AGCATAGCAAGTTTAAATAAGGCT-GTCCGTTATCAACTTGAAAAAGTGGCA CCGAGTCGGTGCTTTTTTTGGAATAAAGATTGTGTGAGCAGCC-GCATTACC TACGATGGTAACCAAAGCTGATTGACTGGGATGCTTT | 13 |
| 34 | AGCATAGCAAGTTTAAATAAGGCTAGTCCGTTATCAACTTGAAAAAGTGGCA -CGAGTCGGTGCTTTTTTTGGAATAAAGATTGTGTGAGCAGCCTGCATTACC TA-GATGGTAACCAAAGCTGATTGACTGGGATGCTTT | 12 |
| 35 | AGCATAGCAAGTTTAAATAAGGCTAGTCCGTT-TCAACTTGAAAAAGTGGCA CCGAGTCGGTGCTTTTTTTGG-ATAAAGATTGTGTGAGCAGCCTGCATTACC TGGTAACCAAAGCTGATTGACTGGGATGCTTT | 11 |
| 36 | AGCATAGCAAGTTTAAATAAGGCTAGTCCGTTATCAACTTGAAAAAGTGGCA C--AGTCGGTGCTTTTTTTGGAATAAAGATTGTGTGAGCAGCCTGCATTACC TA-GATGGTAACCAAAGCTGATTGACTGGGATGCTTT | 10 |
| 37 | AGCATAGCAAGTTTAAATAAGGCTAGTCCGTTATCAACTTGAAAAAGTGGCA CCGAGTCGGTGCTTTTTTTGGAATAAAGA-TGTGTGAGCAGCCTGC -ACGATGGTAACCAAAGCTGATTGACTGGGATGCTTT | 9 |
| 38 | AGCATAGCAAGTTTAAATAAGGCTAGTCCGTTATCAACTTGAAAAAGTGGCA CCGAG-CGGTGCTTTTTTTGGAATAAAGATTGTGTGAGCAGCCTGCATTACC TACG-TGGTAACCAAAGCTGATTGACTGGGATGCTTT | 9 |

TABLE 2-continued

Edited SENSR ™ Sequences

| SEQ ID NO: | Edited SENSR ™ Sequence | # of times observed |
|---|---|---|
| 39 | AGCATAGCAAGTTTAAATAAGGCTAGTCCGTTATCAACTTGAAAAAGTGGCA CCGAGTCGGTGCTTTTTTTGGAATAAAGATTGTGTGAGC-GCCTGCATTACC TACGATGGTAACC-AAGCT-ATTGACTGGGATGCTTT | 9 |
| 40 | AGCATAGCAAGTTTAAATAAGGCTAGTCCGTT-TCAACTTGAAAAAGTGGCA CCGAGTCGGTGCTTTTTTTGGAATAAAGATTGTGTGAGCAGCCTGCATTACC TA-GATGGTAACCAAAGCTGATTGACTGGGATGCTTT | 7 |
| 41 | AGCATAGCAAGTTTAAATAAGGCTAGTCCGTTATCAACT-AAAAAGTGGCA CCGAGTCGGTGCTTTTTTTGGAATAAAGATTGTGTGAGCAG-CTGCATTACC TACGATGGTAACCAAAGCTGATTGACTGGGATGCTTT | 7 |
| 42 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC -ACGATGGTAACCAAAGCTGATTGACTGGGATGCTTT | 7 |
| 43 | AGCATAGCAAGTTTAAATAAGGCTAGTCCGTTAT---CTTGAAAAAGTGGCA CCGAGTCGGTGCTTTTTTTGGAATAAAGATTGTGTGAGCAGCCTGCATTACC TACGATGGTAACCAAAGCTGATTGACTGGGATGCTTT | 6 |
| 44 | AGCATAGCAAGTTTAAATAAGGCTAGTCCGTTATCAACTTGAAAAAGTGGCA CCG-GTCGGTGCTTTTTTTGGAATAAAGATTGTGTGAG-AGCCTGCATTACC TACGATGGTAACCAAAGCTGATTGACTGGGATGCTTT | 6 |

Day 4

| 45 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TACGATGGTAACCAAAGCTGATTGACTGGGATGCTTT | 85 |
| 46 | AGCATAGCAAGTTTAAATAAGGCTAGTCCGTTATCAACTTGAAAAAGTGGCA CCGAGTCGGTGCTTTTTTTGGAAT-AAGATTGTGTGAGCAGCCTGCATTACC --CGATGGTAACCAAAGCTGATTGACTGGGATGCTTT | 19 |
| 47 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCT-CATTACC TACGATGGTAACCAAAGCTGATTGACTGGGATGCTTT | 17 |
| 48 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TA--ATGGTAACCAAAGCTGATTGACTGGGATGCTTT | 10 |
| 49 | AGCATAGCAAGTTTAAATAAGGCTAGTCCGTTATCAACTTG-AAAAGTGGCA CCGAGTCGGTGCTTTTTTTGGAATAAAGATTGTGTGAGCAGCCTGCATTACC TACGATGGTAACCAAAGCTGATTGACTGGGATGCTTT | 9 |
| 50 | AGCATAGCAAGTTTAAATAAGGCTAGTCCGTTATCAACTTGAAAAAGTGG-- -CGAGTCGGTGCTTTTTTTGGAATAAAGATTGTGTGAGCAGCCTGCATTACC TACGATGGTAACCAAAGCTGATTGACTGGGATGCTTT | 9 |
| 51 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGC-TTACC TACGATGGTAACCAAAGCTGATTGACTGGGATGCTTT | 8 |
| 52 | AGCATAGCAAGTTTAAATAAGGCTAGTCCGTTATCAACTTGAAAAAGTGGCA CCGAGTCGGTGCTTTTTTTGGAATAAAGATTGTG-GAGCAGCCTGCATTA- CTACGATGGTAACCAAAGCTGATTGACTGGGATGCTTT | 8 |
| 53 | AGCATAGCAAGTTTAAATAAGGCTAGTCCGTTAT---CTTGAAAAAGTGGCA CCGAGTCGGTGCTTTTTTTGGAATAAAGATTGTGTGAGCAGCCTGCATTACC TACGATGGTAACCAAAGCTGATTGACTGGGATGCTTT | 7 |
| 54 | AGCATAGCAAGTTTAAATAAGGCTAGTCC-TTATCAACTTGAAAAAGTGGCA CCGAGTCGGTGCTTTTTTTGGAATAAAGATTGTGTGAGCAGCCTGCAT-CC TACGATGGTAACCAAAGCTGATTGACTGGGATGCTTT | 6 |
| 55 | AGCATAGCAAGTTTAAATAAGGCTAGTCCGTTATCAACTTGAAAAAGTGGCA CCGAGTC-GTGCTTTTTTTGGAATAAAGATTGTGTGAGCAGCCTGCATTACC TACGATGGTAACCAAAGCTGATTGACTGGGATGCTTT | 6 |
| 56 | AGCATAGCAAGTTTAAATAAGGCTAGTCCGTTATCAACTTGAAAAAGTGGCA CCGAGTCGGTGCTTTTTTTGGAATAAAGATTGTGTGAGCAGCCTGCATTACC TA-GATGGTAACCAAAGCTGATTGACTGGGATGCTTT | 6 |

TABLE 2-continued

Edited SENSR™ Sequences

| SEQ ID NO: | Edited SENSR™ Sequence | # of times observed |
|---|---|---|
| 57 | AGCATAGCAAGTTTAAATAAGGCTAGTCCGTTATCAACTTGAAAAAGTGGCA-CGAGTCGGTGCTTTTTTTGGAATAAAGATTGTGTGAGCAGCCTGCATTACCTACGATGGTAACCAAAGCTGATTGACTGGGATGCTTT Plasmid | 6 |
| 58 | AGCATAGCAAGTTTAAATAAGGCTAGTCCGTTATCAACTTGAAAAAGTGGCACCGAGTCGGTGCTTTTTTTGGAATAAAGATTGTGTGAGCAGCCTGCATTACCTACGATGGTAACCAAAGCTGATTGACTGGGATGCTTT | 731 |
| 59 | AGCATAGCAAGTTTAAATAAGGCTAGTCCGTTATCAACTTGAAAAAGTGGCACCGAGTCGGTGCTTTTTTTGGAAT-AAGATTGTGTGAGCAGCCTGCATTACCTACGATGGTAACCAAAGCTGATTGACTGGGATGCTTT | 16 |
| 60 | AGCATAGCAAGTTTAAATAAGGCTAGTCCGTTATCAACTTGAAAAAGTGGCACCGAGTCGGTGCTTTTTTTGGAATAAAGATTGTGTGAGCAGCCTGCATTACCTACGATGGTAACC-AAGCTGATTGACTGGGATGCTTT | 9 |
| 61 | AGCATAGCAAGTTTAAATAAGGCTAGTCCGTTATCAACTTGAAAAAGTGGCACCGAGTCGGTGCTTTTTTTGGAATAAAGATTGTGTGAGCAGCCTGCATTACCTACG-TGGTAACCAAAGCTGATTGACTGGGATGCTTT | 8 |
| 62 | AGCATAGCAAGTTTAAATAAGGCTAGTCCGTTATCAACTTGAAAAAGTGGCACCGAGTCGGTGCTTTTTTTGG-ATAAAGATTGTGTGAGCAGCCTGCATTACCTACGATGGTAACCAAAGCTGATTGACTGGGATGCTTT | 8 |
| 63 | AGCATAGCAAGTTTAAATAAGGCTAGTCCGTTATCAACTTGAAAAAGTGGCACCGAGTCGGTGCTTTTTTTGGAATAAAGATTGTGTGAGCAGCCTGCATTACCTACGATGGTAACCAAAGCTGA-TGACTGGGATGCTTT | 8 |
| 64 | AGCATAGCAAGTTTAAATAAGGCTAGTCCGTTATCAACTTGAAAAAGTGGCACCGAGTCGGTGCTTTTTTTGGAATAAAGATTGTGTGAGCAGCCTGCA-TACCTACGATGGTAACCAAAGCTGATTGACTGGGATGCTTT | 7 |
| 65 | AGCATAGCAAGTTTAAATAAGGCTAGTCCGTTATCAACTTGAAAAAGTGGCACCGAGTCGGTGCTTTTTTTGGAATAAAGATTGTGTGAGC-GCCTGCATTACCTACGATGGTAACCAAAGCTGATTGACTGGGATGCTTT | 7 |
| 66 | AGCATAGCAAGTTTAAATAAGGCTAGTCCGTTATCAACTTGAAAAAGTGGCACCGAGTCGGTGCTTTTTTTGGAATAAAGATTGTGTGAGCAGCCTGCATTACCTACGATGGT-ACCAAAGCTGATTGACTGGGATGCTTT | 7 |
| 67 | AGCATAGCAAGTTTAAATAAGGCTAGTCCGTTATCAACTTGAAAAAGTGGCACCGAGTCGGTGCTTTTTTTGGAATAAAGATTGTGTG-GCAGCCTGCATTACCTACGATGGTAACCAAAGCTGATTGACTGGGATGCTTT | 7 |
| 68 | AGCATAGCAAGTTTAAATAAGGCTAGTCCGTTATCAACTTGAAAAAGTGGCACCGAGTCGGTGCTTTTTTTGGAATAAAGA-TGTGTGAGCAGCCTGCATTACCTACGATGGTAACCAAAGCTGATTGACTGGGATGCTTT | 6 |

Figure 5:
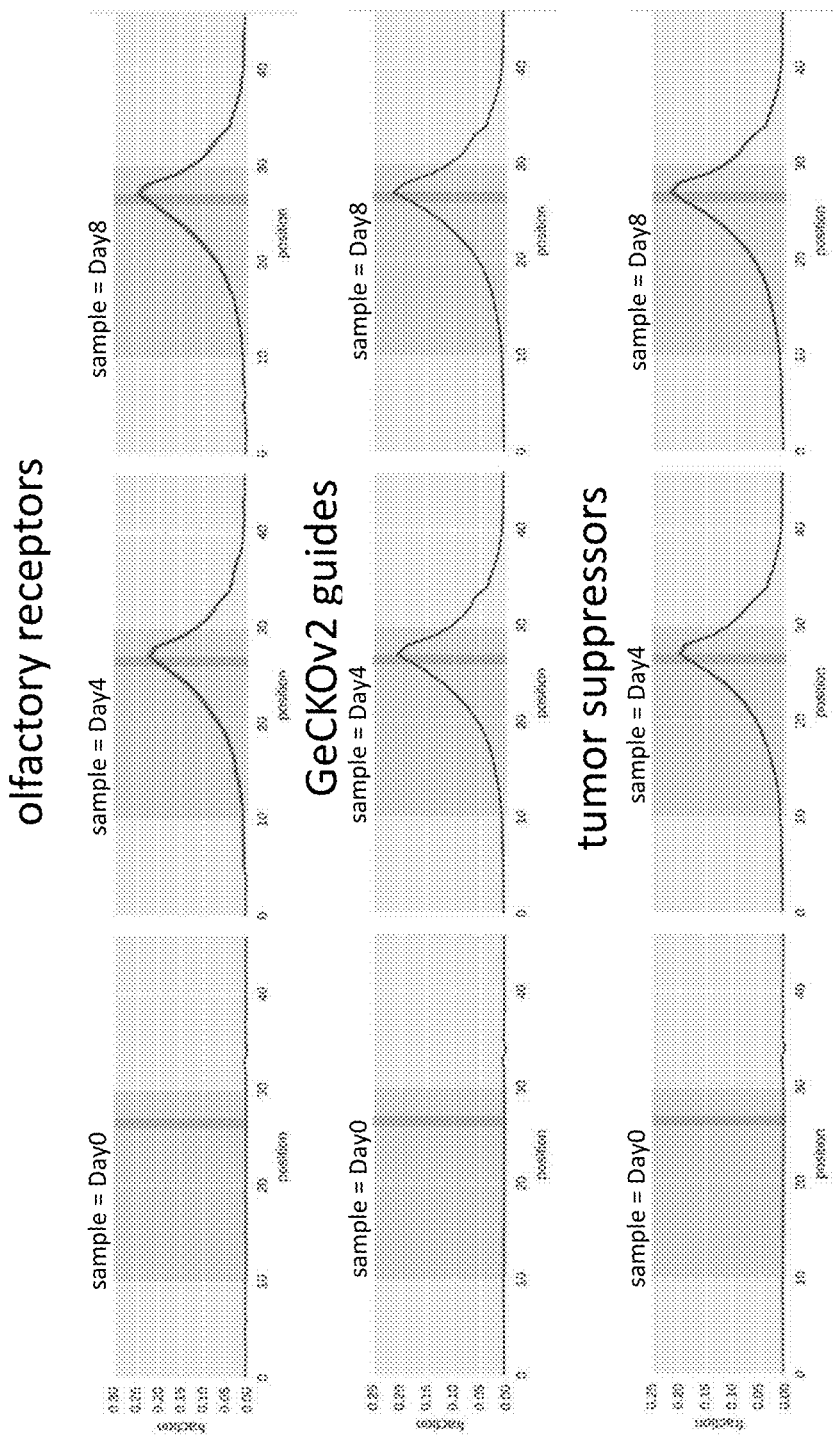
FIG. 5 illustrates CRISPR-SENSR™ data demonstrating efficacy of gRNAs targeting multiple classes of genes (olfactory receptor-targeting guides, GeCKOv2 guides, and tumor suppressor-targeting guides) in the presence or absence of Cas9 expression. The gRNA targeting region is highlighted in light grey, and the predicted cut site is highlighted in darker grey.

Additional studies were performed in RKO cells expressing CRISPR-SENSR™ constructs targeting different classes of genes including olfactory receptors, GeCKOv2 guides (see Doench et al., (2016) Nature Biotechnology 34.184-191), and tumor suppressors (FIG. 5). For each plot, the fraction that each position is deleted is aggregated over all of the gRNAs in that class at that time point. Experiments were also performed in HT1080 cells with essentially identical results. The gRNA targeting region is highlighted in light grey, and the predicted cutting site (−3) is indicated by darker grey highlight. For each class of gene targeted, appreciable deletions within the SENSR™ sequence were only observed in the presence of Cas9. Further, deletions occurred near the expected cutting site regardless of the class of gene targeted. These data indicate that, in addition to functioning in multiple cell lines, CRISPR-SENSR™ constructs are effective at targeting a broad variety of target sequences.

Figure 6:
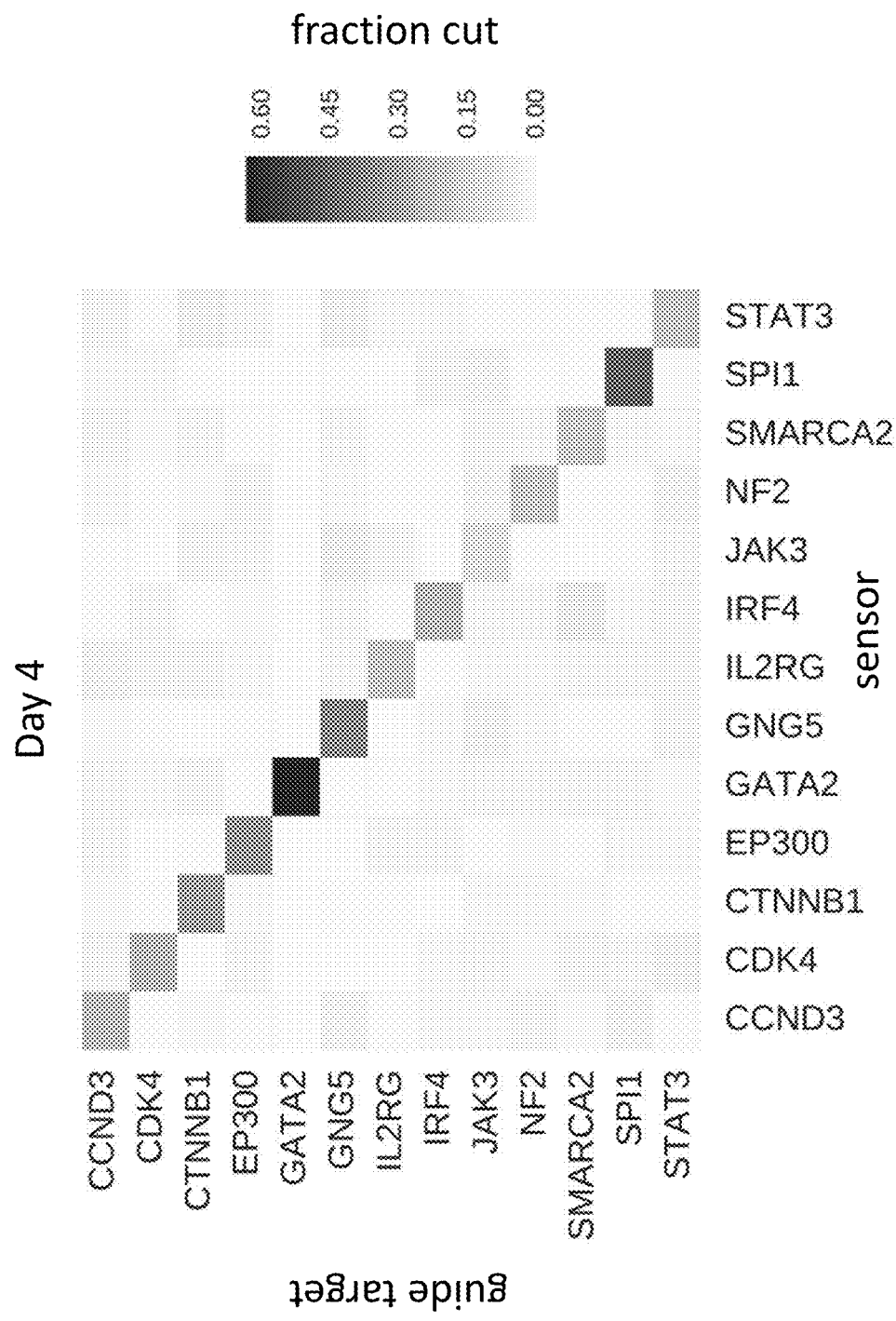
FIG. 6 illustrates a matrix comparing the fraction of cutting in guide targets and the SENSR' sequences for a panel of genes.
Figure 7:
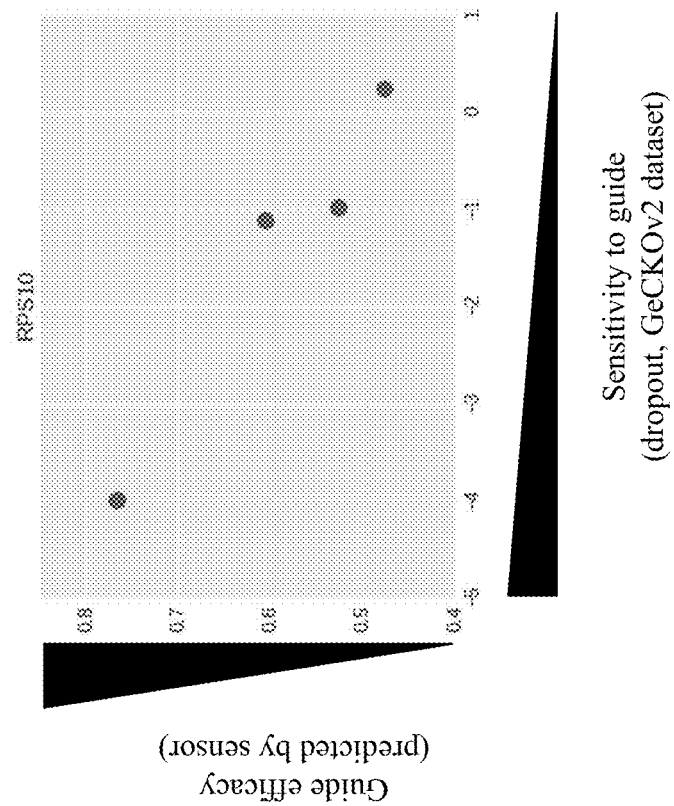
FIG. 7 illustrates a comparison of the cutting efficiency of gRNAs targeting RPL27 compared to a phenotypic read out of cell growth.
Figure 8:
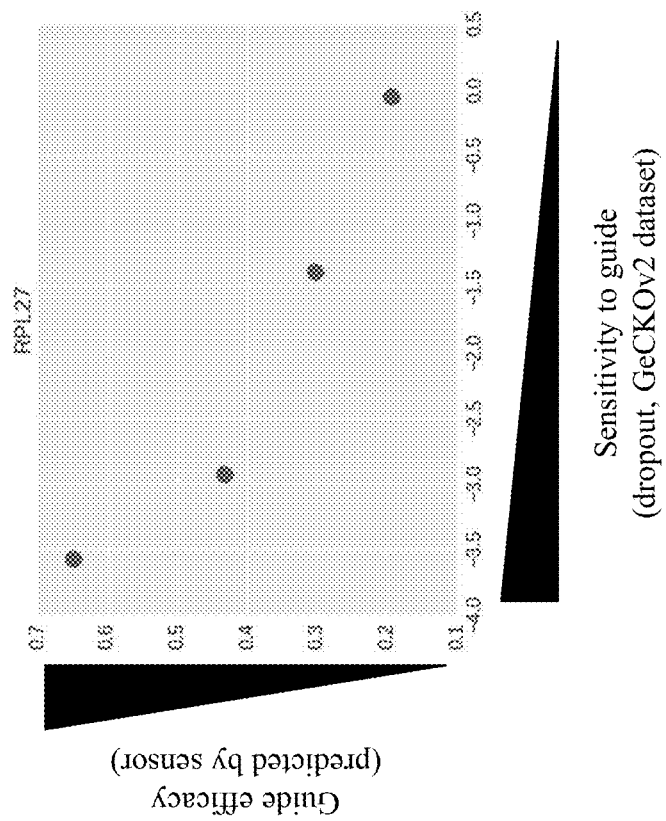
FIG. 8 illustrates a comparison of the cutting efficiency of gRNAs targeting RPS10 compared to a phenotypic read out of cell growth.
Figure 9:
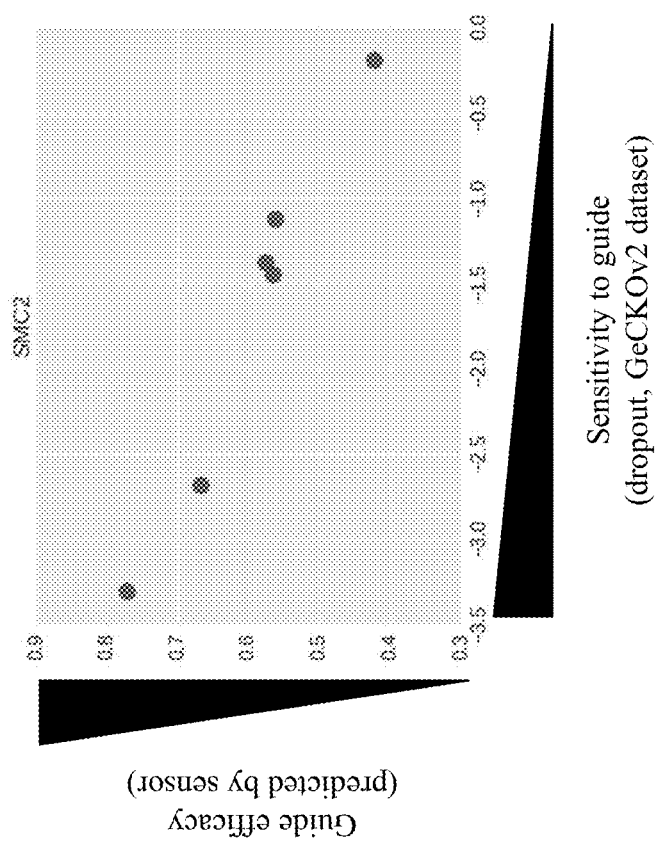
FIG. 9 illustrates a comparison of the cutting efficiency of gRNAs targeting SMC2 compared to a phenotypic read out of cell growth.

Additional analyses were performed to determine the specificity of the gRNA encoded by the CRISPR-SENSR™ construct for the SENSR™ sequence encoded by the CRISPR-SENSR™ constructs. The specificity of the CRISPR-SENSR™ constructs was tested within a panel of 13 genes. Each gRNA was paired with each SENSR™ sequence and the fraction of corresponding reads containing a deletion over the expected cut site was determined. Results are shown in matrix form in FIG. 6. These results demonstrate that significant SENSR™ cutting was only observed when the gRNA target matches the SENSR™ sequence, as indicated by darker blue in FIG. 6. Virtually no cutting was observed with the gRNA target did not match the SENSR™ sequence.

Example 6: CRISPR-SENSR™ Results Predict gRNA Dropout and Enrichment Differences The efficacy of the CRISPR-SENSR™ system at improving existing CRISPR/Cas9 systems was determined. Cutting efficiency of gRNAs directed to four essential genes, RPL27

(FIG. 7), RPS10 (FIG. 8), SMC2 (FIG. 9), and PSMA1 (FIG. 15) and one tumor suppressor gene, AIRD38 (FIG. 16) was determined using the CRISPR-SENSR™ system. This cutting efficacy (or guide efficacy) was compared to a phenotypic readout measuring how the loss of each gene impacts cell growth. For essential genes, the phenotypic readout measuring the impact of gene loss on cell growth is referred to as gRNA "dropout" or depletion, as gRNA-mediated loss of an essential gene is expected to result in cell death, thereby reducing the frequency of that particular gRNA. For tumor suppressor genes, the phenotypic readout measuring the impact of gene loss on cell growth is referred to as gRNA enrichment, as gRNA-mediated loss of a tumor suppressor is expected to result in increased cell proliferation and/or prolonged cell survival, thereby increasing the frequency of that particular gRNA As shown in FIGS. 7-9 and FIGS. 15-16, gRNAs that were demonstrably more efficacious (i.e. demonstrated a higher cutting efficiency) as determined by CRISPR-SENSR™ had a larger impact on the growth of the cell.

Figure 10:
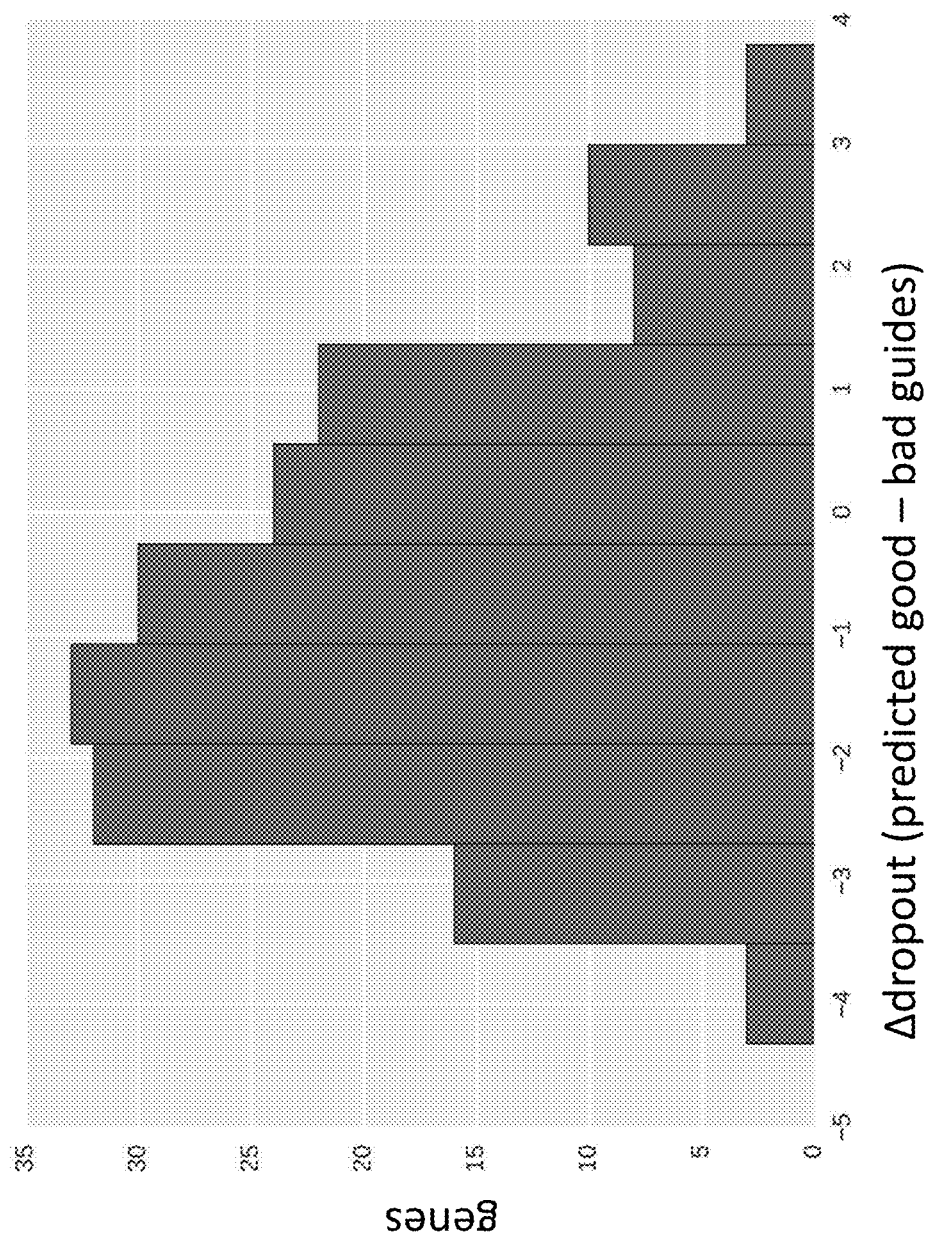
FIG. 10 illustrates the Δdropout (average # of predicted good guides—average # of predicted bad guides). For each gene in the SENSR™ analyses that contained at least 1 good and 1 bad guide, the difference in sensitivity is plotted.

In an additional analysis, gRNAs were classified as "good" or "bad" based on their cutting activity in CRISPR-SENSR™ analyses. For each gene that contained at least 1 good and 1 bad guide, the distribution of sensitivity differences after subtracting the dropout value for the bad guides from the dropout value for the good guides (Δdropout) was plotted (FIG. 10). More negative values indicated increased activity (phenotypic dropout) to predicted good guides, showing that inferences from the CRISPR-SENSR™ library generalize to phenotypic readouts of the effects of particular gRNAs.

Example 7: Edited CRISPR-SENSR™ Improves Signal: Noise Ratio

Figure 11:
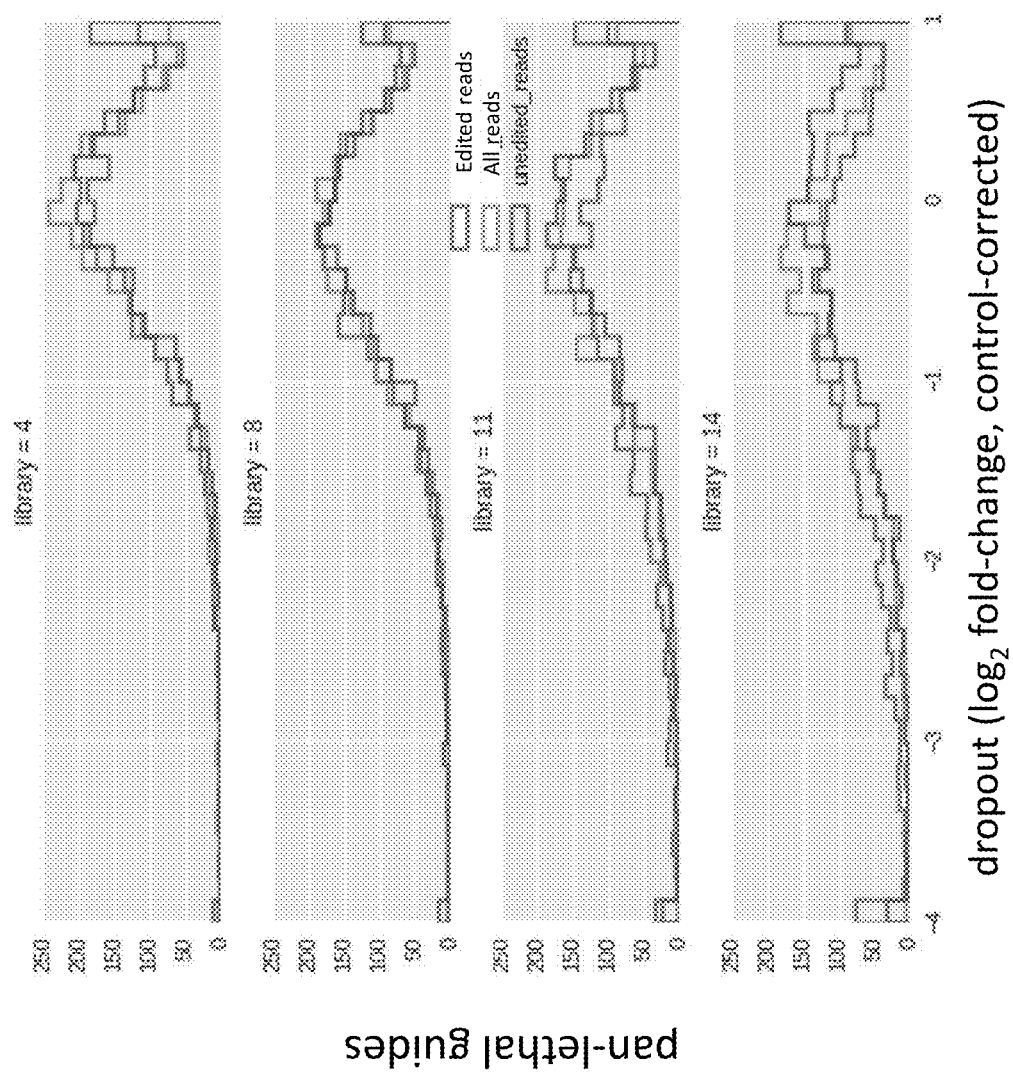
FIG. 11 illustrates the effects changes in the dropout values when all reads are considered, when only edited SENSR™ reads are considered, or when only unedited reads are considered.

In addition to providing information about a given gRNA's activity and cutting profile, the presence of an edited or altered SENSR™ sequence can serve as a proxy for functional Cas9 expression. As such, cells without an altered SENSR™ sequence can be filtered out, thus reducing the background noise of the system. A CRISPR-SENSR™ library co-expressed with Cas9 in RKO cells and multiple time points were taken for sequence analysis. Experiments were also performed in HT1080 cells with essentially identical results. For each time point, the $log_2$ fold-change of the dropout was calculated considering one of the following groups: all reads, edited SENSR™ reads, or unedited SENSR™ reads (FIG. 11). As shown in FIG. 11, the group of gRNAs that resulted in an edited SENSR™ read resulted in a shift in the calculated dropout value (e.g. resulted in a more negative dropout value). These data indicate that libraries comprised of gRNAs that result in edited SENSR™ sequences decreased the dropout value, indicating an overall increased sensitivity to the gRNA.

Figure 12:
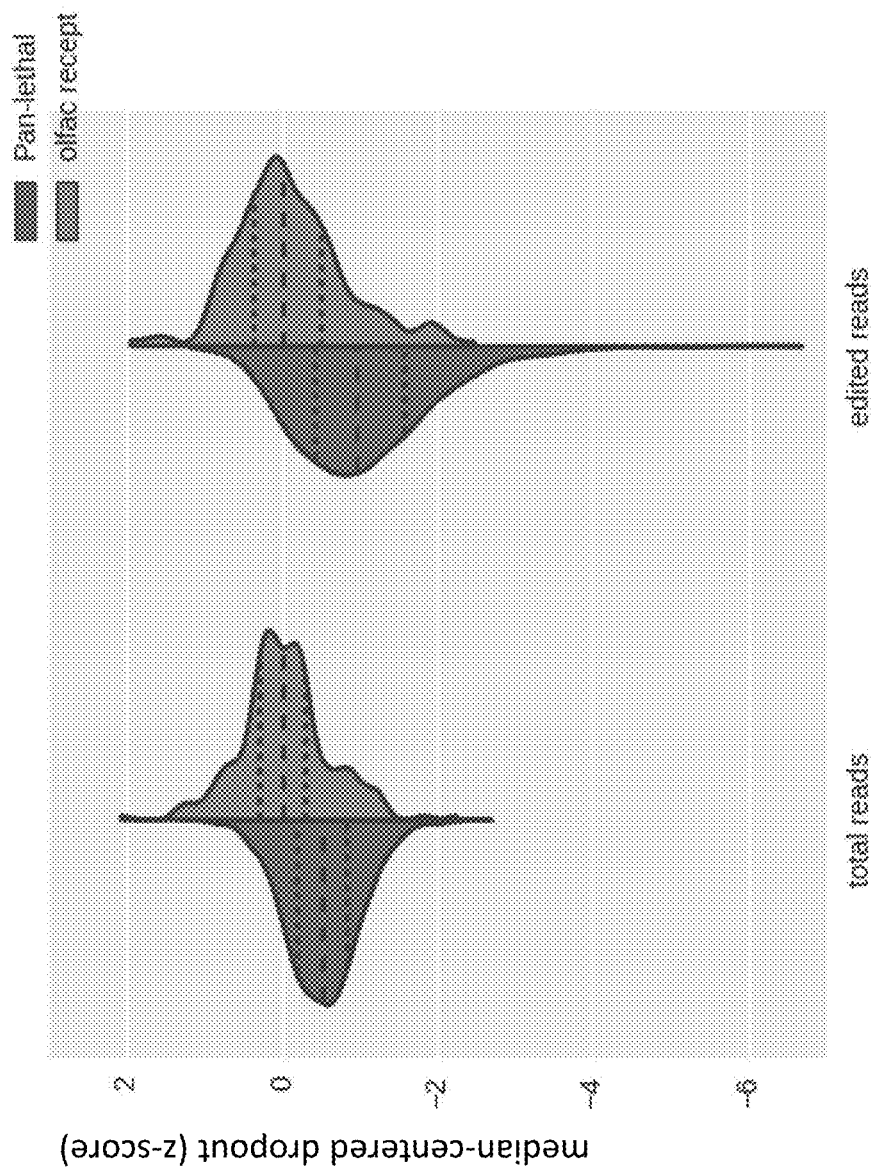
FIG. 12 illustrates the dropout (centered to the median of olfactory receptors) for guides targeting pan-lethal genes is compared the dropout for negative controls (olfactory receptor genes)

Further, the CRISPR-SENSR™ system increased the dynamic range of the screening assays and improved the signal to noise ratio (e.g. increased the differences between the targets being evaluated and the negative controls). A CRISPR-SENSR™ library targeting a sub-set of pan-lethal genes and those targeting olfactory receptors (negative controls) was co-expressed with Cas9 in RKO cells. Experiments were also performed in HT1080 cells with essentially identical results. Dropout was calculated using either all reads or only edited SENSR™ reads. As shown in FIG. 12, utilizing the CRISPR-SENSR™ system dramatically increased the assay's dynamic range and improved the signal-to-noise ratio as noted by an increased difference in the median-centered dropout values.

Example 8: gRNA Mismatch Tolerance

Figure 13:
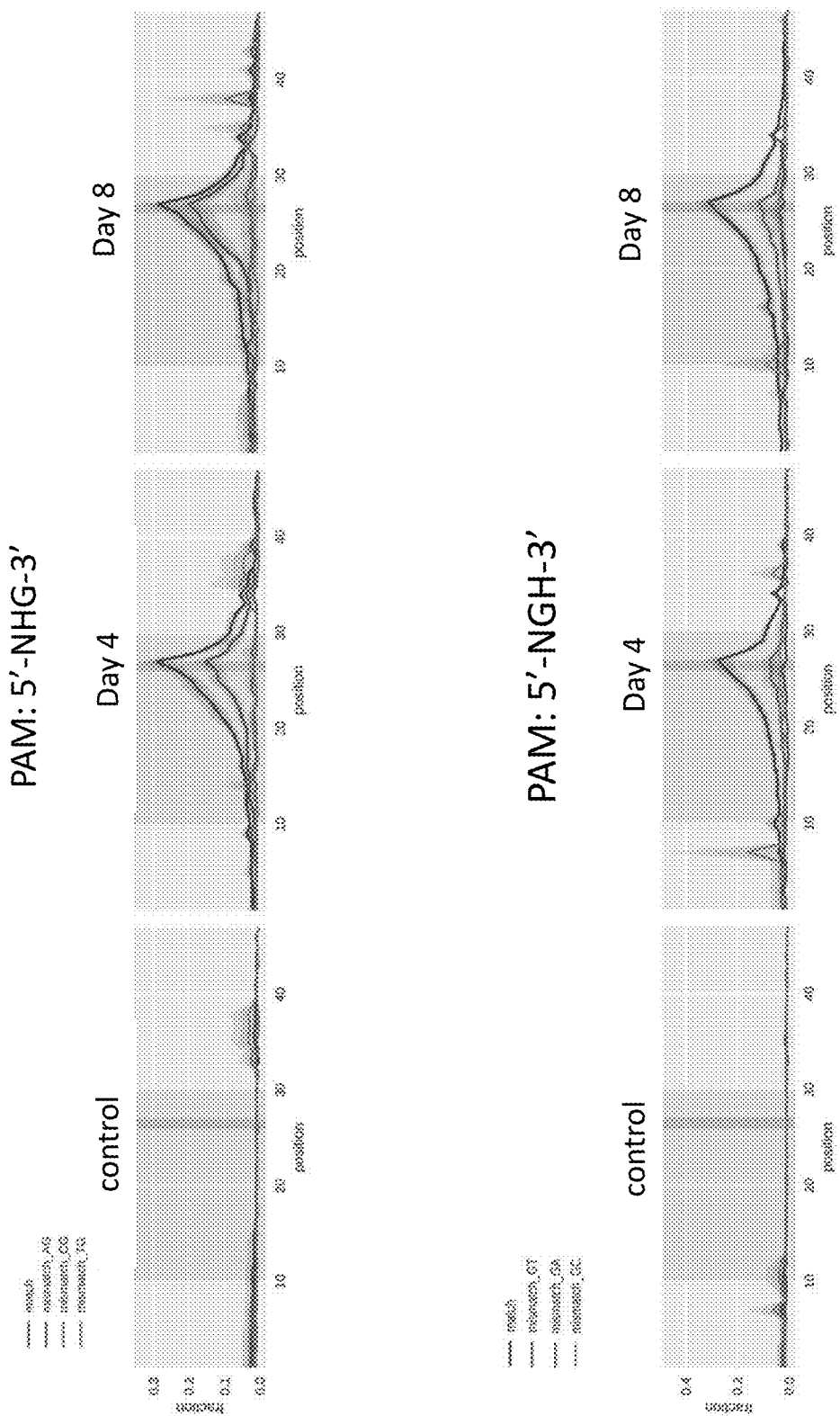
FIG. 13 illustrates CRISPR-SENSR™ data to determine the tolerance of the system to mutations in the PAM transition sequence in the SENSR™ Sequence. The gRNA targeting region is highlighted in light grey, and the predicted cut site is highlighted in darker grey.
Figure 15:
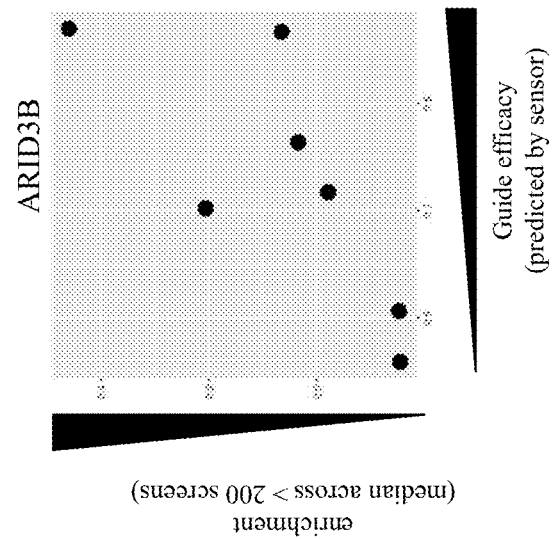
FIG. 15 illustrates a comparison of the cutting efficiency of gRNAs targeting PSMA compared to a phenotypic read out of cell growth.
Figure 16:
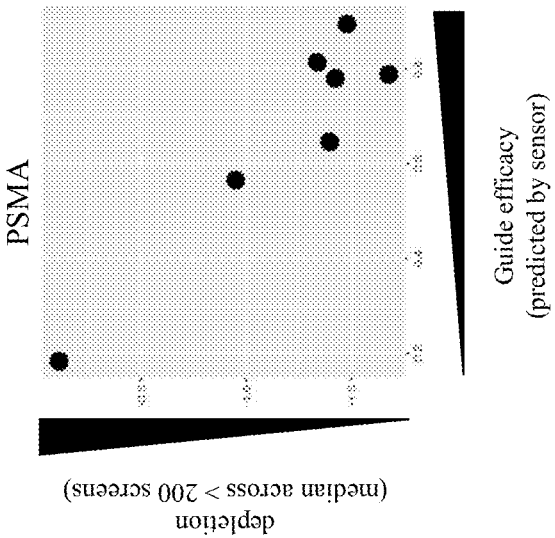
FIG. 16 illustrates a comparison of the cutting efficiency of gRNAs targeting ARID3B compared to a phenotypic read out of cell growth.

Experiments were performed to determine gRNA tolerance for sequence mismatches, both in the PAM transition sequence and the gRNA sequence itself. CRISPR-SENSR™ constructs comprising a mutation in the PAM transition sequence in the SENSR™ Sequence were co-expressed with Cas9 in RKO cells. For each plot, the fraction that each position is deleted is aggregated over all of the gRNAs in that class at that time point. Experiments were also performed in HT1080 cells with essentially identical results. The gRNA targeting region is highlighted in light grey, and the predicted cutting site (−3) is indicated by darker grey highlight. The PAM sequence for spCas9 is 5'-NGG-3', wherein N is any base pair. Mutation of the NGG sequence to either NHG or NGH, wherein H is any base pair other than G (e.g. A, T, or C according to the IUPAC nucleotide codes) resulted in substantially reduced Cas9-mediated cutting compared to the NGG sequence (FIG. 13). As such, transition mismatches in the PAM sequence result in low-level cutting of the target sequence.

Similar experiments were performed wherein mismatches were present in the gRNA targeting sequence. CRISPR-SENSR™ constructs comprising a mutation at the −1, −3 or −4 position in the gRNA sequence were co-expressed with Cas9 in RKO cells. For each plot, the fraction that each position is deleted is aggregated over all of the gRNAs in that class at that time point. Experiments were also performed in HT1080 cells with essentially identical results. The gRNA targeting region is highlighted in light grey, and the predicted cutting site (−3) is indicated by darker grey highlight. These results indicate that some mismatches in the gRNA sequence are tolerated (FIG. 14). Specifically, mismatches that occurred at the −1 position were well-tolerated compared to those that occur at the −4 position.

Example 9: Out-of-Sample Predictive Ability of the CRISPR-SENSR™ System

The CRISPR-SENSR™ system provide out-of-sample predictive ability. A classifier was trained to predict class membership for "good" guides (those displaying cutting efficiency >50%) and "bad" guides (those displaying cutting efficiency <20%), where cutting efficiency was measured by sequencing of the SENSR™ sequence. A search over algorithms and parameter choices was performed and methods were evaluated over 10-fold cross-validation, optimizing the F1 score rather than AUROC because of imbalanced class sizes. The best-performing model using the identified parameters was then trained on the full dataset. Features included in the model:
melting temperature of the guide (continuous)
micro-homology (continuous, as calculated in [1])
GC content of the guide (continuous)
GC content of the −10 to +8 positions (continuous, where 0 corresponds to the end of the guide and −3 corresponds to the cut site)
Overlapping a protein domain (PFAM domain) (boolean)
Overlapping coding sequence (boolean)
Overlapping a splice site (Boolean)
nucleotide at each position from −10 to +8 (one-hot encoding of each base)
type of base at each position from −10 to +8 (either purine or pyrimidine, one-hot encoded)

dinucleotide at each position from −10 to +8 (one-hot encoding of each base)

pairs of base types at each position from −10 to +8 (either purine or pyrimidine, one-hot encoded)

trinucleotide at each position from −10 to +8 (one-hot encoding of each base)

triplets of base types at each position from −10 to +8 (either purine or pyrimidine, one-hot encoded)

Figure 17:
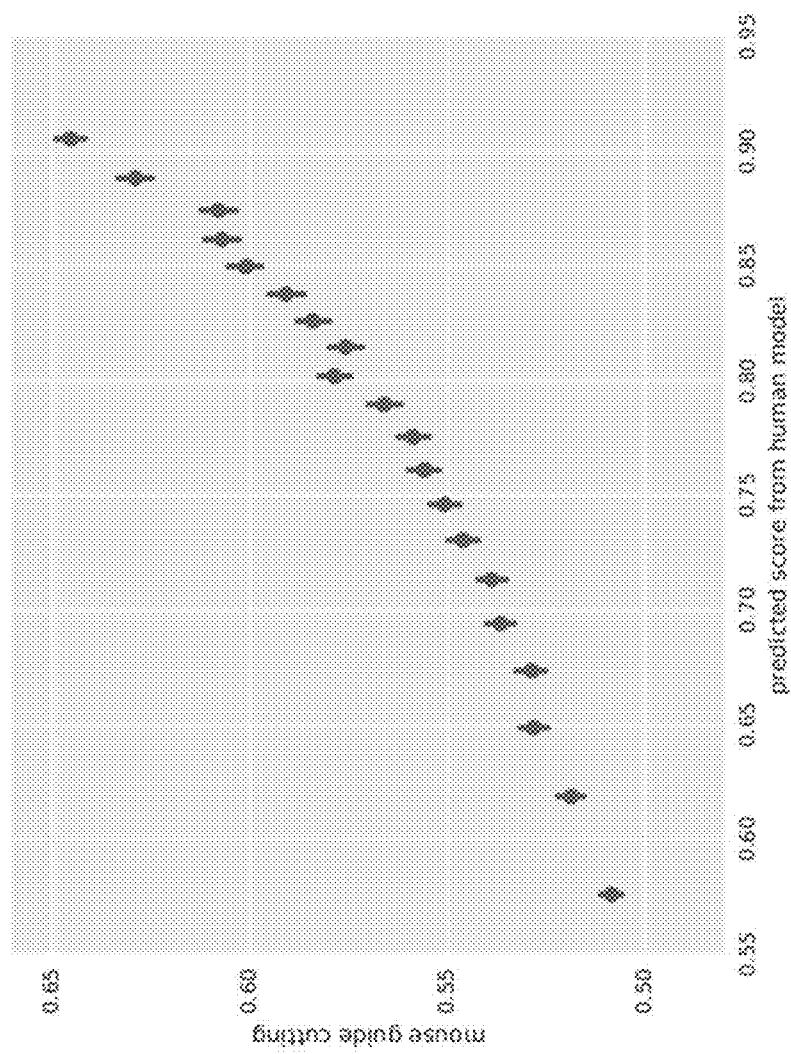
FIG. 17 illustrates the ability of a model trained on a human CRISPR-SENSR™ library to predict performance of gRNAs targeting murine genes.

This model facilitated the prediction of cutting efficiency for new guides that are not included in the SENSR™ library used to train the model. The best performing model achieved an F1 score of >0.8 and an AUROC of 0.9, suggesting that it was not a replacement for gRNA identification using a CRISPR-SENSR™ library. Nevertheless, a model trained using human gRNA sequences demonstrated considerable predictive ability for mouse sequences, as shown in FIG. 17, where the more confident the model was that a guide was a "good" guide, the higher the empirical cutting efficiency (as measured by a separate mouse CRISPR-SENSR™ construct, data not shown). Thus, the present invention provides materials and methods that are useful for more efficient selection of gRNAs for use in genome editing, with a higher predictive power/level of confidence than can otherwise be achieved with previously described methods.

The invention claimed is:

1. A method of preparing an optimized guide RNA (gRNA) library comprising;
   (a) introducing a library of nucleic acid constructs into a population of cells modified to express a Cas9 protein, wherein each construct comprises a gRNA sequence and a sensor sequence, wherein the sensor sequence comprises the corresponding gRNA target sequence;
   (b) culturing said cells from step (a) under conditions permitting the expression of said gRNA and said Cas9 protein;
   (c) amplifying the nucleic acid constructs sequences by polymerase chain reaction (PCR) from the cells of step (b) to obtain a plurality of amplicons, wherein each amplicon comprises the gRNA sequence and the sensor sequence;
   (d) sequencing said plurality of amplicons;
   (e) determining a pattern of alterations in the sensor sequence in each of the amplicons; and
   (f) identifying a population of gRNAs that produce a desired pattern of alterations in the sensor sequence, wherein the population of cells is modified with a nucleic acid encoding the Cas9 protein, and wherein the nucleic acid encoding the Cas9 protein mRNA is introduced into the population of cells by electroporation.

2. The method of claim 1, wherein the library of nucleic acid constructs encode a genome wide or a sub-genome wide library of gRNAs.

3. The method of claim 1, wherein the nucleic acid encoding a Cas9 protein is encoded by a viral vector.

4. The method of claim 3, wherein the viral vector is a lentiviral vector and is introduced at a titer of at least about $1 \times 10^6$ infectious particles/mL.

5. The method of claim 1, wherein the Cas9 protein is a dCas9 protein.

6. The method of claim 5, wherein the dCas9 protein is fused with a transcriptional repressor domain.

7. The method of claim 5, wherein the dCas9 protein is fused with a transcriptional activator.

8. The method of claim 5, wherein the dCas9 protein is fused with a heterologous protein domain.

9. The method of claim 1, wherein the Cas9 protein is a nickase mutant of Cas9.

10. The method of claim 1, wherein the expression of the nucleic acid encoding a Cas9 protein is under the control of an inducible gene element.

11. The method of claim 1, wherein the population of cells are mammalian cells.

12. The method of claim 1, wherein the sensor sequence is a nucleic acid sequence from a mammalian genome.

13. The method of claim 12, wherein the sensor sequence is from a human genome and the gRNAs identified in step (e) produce the desired pattern of alterations in the human sensor sequence.

14. The method of claim 1, wherein the nucleic acid construct is encoded by a lentiviral vector, and wherein the lentiviral vector is introduced at a titer of at least about $1 \times 10^6$ infectious particles/mL.

15. The method of claim 1, wherein the nucleic acid construct is under the control of an inducible gene element.

16. The method of claim 1, wherein the sequencing comprises high throughput sequencing.

17. The method of claim 1, wherein the desired pattern of alterations is selected from a group consisting of insertions in the sensor sequence, deletions in the sensor sequence, and mutations in the sensor sequence.

18. The method of claim 1, further comprising introducing a nucleic acid sequence encoding a repair template into the transduced population of cells.

19. The method of claim 1, wherein the desired pattern of alterations are a result of a mechanism selected from the group consisting of non-homologous end-joining (NHEJ) and homology-directed repair (HDR).

20. The method of claim 1, further comprising;
   (g) amplifying an endogenous target nucleic acid sequence by PCR from the cells of step (c) to obtain a plurality of endogenous target amplicons;
   (h) sequencing said endogenous target amplicons;
   (i) determining a pattern of alterations in said endogenous target sequence;
   (j) comparing the pattern of alterations in the endogenous target sequence with the pattern of alterations in the sensor sequence; and
   (k) determining a population of gRNAs that produce a desired pattern of alterations in both the endogenous target sequence and the sensor sequence.

21. The method of claim 20, wherein the desired pattern of alterations in the endogenous target sequence and the sensor sequence is selected from the group consisting of insertions, deletions, and mutations.

22. The method of claim 1, further comprising:
   (g) quantifying a transcription level of an endogenous target sequence and/or sensor sequence from the population of cells of step (c) by quantitative PCR (qPCR);
   (h) comparing the transcription level of step (g) to a transcription level of the endogenous target sequence and/or sensor sequence obtained from a control cell population by qPCR;

(i) determining a pattern of transcriptional changes in the endogenous target sequence and/or sensor sequence; and
(j) determining a population of gRNAs that produce a desired pattern of transcriptional changes in the endogenous target sequence and/or sensor sequence.

* * * * *

SEQUENCE LISTING

```
<160> NUMBER OF SEQ ID NOS: 68

<210> SEQ ID NO 1
<211> LENGTH: 141
<212> TYPE: DNA
<213> ORGANISM: Artificial Sequence
<220> FEATURE:
<223> OTHER INFORMATION: Synthesized in Lab

<400> SEQUENCE: 1
agcatagcaa gtttaaataa ggctagtccg ttatcaactt gaaaaagtgg caccgagtcg     60 gtgcttttt tggaataaag attgtgtgag cagcctgcat tacctacgat ggtaaccaaa    120
gctgattgac tgggatgctt t                                              141

<210> SEQ ID NO 2
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 2
agcatagcaa gtttaaataa ggctagtccg ttatcaactt gaaaaagtgg caccgagtcg     60 gtgcttttt tggaataaag attgtgtgag cagcctgcat tacctagatg gtaaccaaag    120
ctgattgact gggatgcttt                                                140

<210> SEQ ID NO 3
<211> LENGTH: 132
<212> TYPE: DNA
<213> ORGANISM: Artificial Sequence
<220> FEATURE:
<223> OTHER INFORMATION: Synthesized in Lab

<400> SEQUENCE: 3
agcatagcaa gtttaaataa ggctagtccg ttatcaactt gaaaaagtgg caccgagtcg     60 gtgcttttt tggaataaag attgtgtgag cagcctgcga tggtaaccaa agctgattga    120
ctgggatgct tt                                                        132

<210> SEQ ID NO 4
<211> LENGTH: 128
<212> TYPE: DNA
<213> ORGANISM: Artificial Sequence
<220> FEATURE:
<223> OTHER INFORMATION: Synthesized in Lab
```

-continued

```
<400> SEQUENCE: 4
agcatagcaa gtttaaataa ggctagtccg ttatcaactt gaaaaagtgg caccgagtcg      60 gtgcttttt  tggaataaag attgtgtgag cagcctgcat aaccaaagct gattgactgg     120
gatgcttt                                                              128

<210> SEQ ID NO 5
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 5
agcatagcaa gtttaaataa ggctagtccg ttatcaactt gaaaaagtgg caccgagtcg      60 gtgcttttt  tggaataaag attgtgtgag cagcctgcat taccacgatg gtaaccaaag    120
ctgattgact gggatgcttt                                                 140

<210> SEQ ID NO 6
<211> LENGTH: 120
<212> TYPE: DNA
<213> ORGANISM: Artificial Sequence
<220> FEATURE:
<223> OTHER INFORMATION: Synthesized in Lab

<400> SEQUENCE: 6
agcatagcaa gtttaaataa ggctagtccg ttatcaactt gaaaaagtgg caccgagtcg      60 gtgcttttt  tggaataaag ttgtgtgatg gtaaccaaag ctgattgact gggatgcttt    120

<210> SEQ ID NO 7
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 7
agcatagcaa gtttaaataa ggctagtccg ttatcttgaa aaagtggcac cgagtcggtg      60 cttttttgg  aataaagatt gtgtgagcag cctgcattac ctacgatggt aaccaaagct    120
gattgactgg gatgcttt                                                   138

<210> SEQ ID NO 8
<211> LENGTH: 128
<212> TYPE: DNA
<213> ORGANISM: Artificial Sequence
<220> FEATURE:
<223> OTHER INFORMATION: Synthesized in Lab

<400> SEQUENCE: 8
agcatagcaa gtttaaataa ggctagtccg ttatcaactt gaaaaagtgg caccgagtcg      60 gtgcttttt  tggaataaga ttgtgtgagc agccgatggt aaccaaagct gattgactgg     120
gatgcttt                                                              128

<210> SEQ ID NO 9
<211> LENGTH: 128
<212> TYPE: DNA
<213> ORGANISM: Artificial Sequence
<220> FEATURE:
<223> OTHER INFORMATION: Synthesized in Lab
```

<400> SEQUENCE: 9
agcatagcaa gtttaaataa ggctagtccg ttatcaactt gaaaaagtgg caccgagtcg    60 gtgcttttt tggaataaag attgtgtgag cagcctgcgt aaccaaagct gattgactgg    120
gatgcttt                                                             128

<210> SEQ ID NO 10
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 10
agcatagcaa gtttaaataa ggctagtccg ttatcaactt gaaaaatggc accgagtcgg    60
tgcttttttt ggaataaaga ttgtgtgagc agcctgcatt acctacgatg gtaaccaaag    120
ctgattgact gggatgcttt                                                140

<210> SEQ ID NO 11
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 11
agcatagcaa gtttaaataa ggctagtccg ttatcaactt gaaaaagtgg caccgagtcg    60 gtgcttttt tggaataaag attgtgtgag cagcctgcat tacctacgat gtaaccaaag    120
ctgattgact gggatgcttt                                                140

<210> SEQ ID NO 12
<211> LENGTH: 141
<212> TYPE: DNA
<213> ORGANISM: Artificial Sequence
<220> FEATURE:
<223> OTHER INFORMATION: Synthesized in Lab

<400> SEQUENCE: 12
agcatagcaa gtttaaataa ggctagtccg ttatcaactt gaaaaagtgg caccgagtcg    60 gtgcttttt tggaataaag attgtgtgag cagcctgcat tacctacgat ggtaaccaaa    120
gctgattgac tgggatgctt t                                              141

<210> SEQ ID NO 13
<211> LENGTH: 141
<212> TYPE: DNA
<213> ORGANISM: Artificial Sequence
<220> FEATURE:
<223> OTHER INFORMATION: Synthesized in Lab

<400> SEQUENCE: 13
agcatagcaa gtttaaataa ggctagtccg ttatcaactt gaaaaagtgg caccgagtcg    60 gtgcttttt tggaataaag attgtgtgag cagcctgcat tacctacgat ggtaaccaaa    120
gctgattgac tgggatgctt t                                              141

<210> SEQ ID NO 14
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 14
agcatagcaa gtttaaataa ggctagtccg ttatcaactt gaaaaagtgg caccgagtcg     60 gtgcttttt ggaataaaga ttgtgtgagc agcctgcatt acctacgatg gtaaccaaag    120
ctgattgact gggatgcttt                                                140

<210> SEQ ID NO 15
<211> LENGTH: 141
<212> TYPE: DNA
<213> ORGANISM: Artificial Sequence
<220> FEATURE:
<223> OTHER INFORMATION: Synthesized in Lab

<400> SEQUENCE: 15
agcatagcaa gtttaaataa ggctagtccg ttatcaactt gaaaaagtgg caccgagtcg     60 gtgcttttt tggaataaag attgtgtgag cagcctgcat tacctacgat ggtaaccaaa    120
gctgattgac tgggatgctt t                                              141

<210> SEQ ID NO 16
<211> LENGTH: 128
<212> TYPE: DNA
<213> ORGANISM: Artificial Sequence
<220> FEATURE:
<223> OTHER INFORMATION: Synthesized in Lab

<400> SEQUENCE: 16
agcatagcaa gtttaaataa ggctagtccg ttatcaactt gaaaaagtgg caccgagtcg     60 gtgcttttt tggaataaag attgtgtgag cagcctgcat aaccaaagct gattgactgg    120
gatgcttt                                                             128

<210> SEQ ID NO 17
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 17
agcatagcaa gtttaaataa ggctagtccg ttatcaactt gaagtggcac cgagtcggtg     60 cttttttgg aataaagatt gtgtgagcag cctgcattac ctacgatggt aaccaaagct    120
gattgactgg gatgcttt                                                  138

<210> SEQ ID NO 18
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 18
agcatagcaa gtttaaataa ggctagtccg ttatcaactt gaaaaagtgg caccgagtcg     60 gtgcttttt tggaataaag attgtgtgag cagcctgcat tacctacgat gtaaccaaag    120
ctgattgact gggatgcttt                                                140

<210> SEQ ID NO 19
<211> LENGTH: 136
<212> TYPE: DNA
<213> ORGANISM: Artificial Sequence
<220> FEATURE:

<223> OTHER INFORMATION: Synthesized in Lab

<400> SEQUENCE: 19

| agcatagcaa gtttaaataa ggctagtccg ttatcaactt gaaaaagtgg caccgagtcg | 60 |
| gtgctttttt tggaataaag attgtgtgag cagcctgcat tacctagtaa ccaaagctga | 120 |
| ttgactggga tgcttt | 136 |

<210> SEQ ID NO 20
<211> LENGTH: 128
<212> TYPE: DNA
<213> ORGANISM: Artificial Sequence
<220> FEATURE:
<223> OTHER INFORMATION: Synthesized in Lab

<400> SEQUENCE: 20

| agcatagcaa gtttaaataa ggctagtccg ttatcaactt gaaaaagtgg caccgagtcg | 60 |
| gtgctttttt tggaataaag attgtgtgag cagcctgcgt aaccaaagct gattgactgg | 120 |
| gatgcttt | 128 |

<210> SEQ ID NO 21
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 21

| agcatagcaa gtttaaataa ggctagtccg ttatcaactt gaaaaagtgg caccgagtcg | 60 |
| gtgctttttt tggaataaag attgtgtgag cagcctgcat tacctacggg taaccaaagc | 120 |
| tgattgactg ggatgcttt | 139 |

<210> SEQ ID NO 22
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 22

| agcatagcaa gtttaaataa ggctagtccg ttatcaactt gaaaaagtgg caccgagtcg | 60 |
| gtgctttttt tggaataaag attgtgtgag cagcctgcat tacctacatg gtaaccaaag | 120 |
| ctgattgact gggatgcttt | 140 |

<210> SEQ ID NO 23
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 23

| agcatagcaa gtttaaataa ggctagtccg ttatcaactt gaaaaagtgg caccgagtcg | 60 |
| gtgctttttt tggaataaag attgtgtgag cagcctgcat taccacgatg gtaaccaaag | 120 |
| ctgattgact gggatgcttt | 140 |

<210> SEQ ID NO 24
<211> LENGTH: 140
<212> TYPE: DNA
<213> ORGANISM: Artificial Sequence

```
<220> FEATURE:
<223> OTHER INFORMATION: Synthesized in Lab

<400> SEQUENCE: 24
agcatagcaa gtttaaataa ggctagtccg ttatcaactt gaaaaagtgg caccgagtcg    60
gtgctttttt tggaataaag atgtgtgagc agcctgcatt acctacgatg gtaaccaaag   120
ctgattgact gggatgcttt                                               140

<210> SEQ ID NO 25
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 25
agcatagcaa gtttaaataa ggctagtccg ttatcaactt gaaaaagtgg caccgagtcg    60
gtgctttttt tggaataaag ttgtgtgagc agcctgcata cctacgatgg taaccaaagc   120
tgattgactg ggatgcttt                                                139

<210> SEQ ID NO 26
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 26
agcatagcaa gtttaaataa ggctagtccg ttatcaactt gaaaaagtgg caccgagtcg    60
gtgctttttt tggaataaag attgtgtgag cagcctgcat tacctagatg gtaaccaaag   120
ctgattgact gggatgcttt                                               140

<210> SEQ ID NO 27
<211> LENGTH: 126
<212> TYPE: DNA
<213> ORGANISM: Artificial Sequence
<220> FEATURE:
<223> OTHER INFORMATION: Synthesized in Lab

<400> SEQUENCE: 27
agcatagcaa gtttaaataa ggctagtcct tatcaacttg aaaaagtggc accgagtcgg    60 tgctttttt ggaataaaga ttgtgtgagc agcctgcata ccaaagctga ttgactggga   120
tgcttt                                                              126

<210> SEQ ID NO 28
<211> LENGTH: 135
<212> TYPE: DNA
<213> ORGANISM: Artificial Sequence
<220> FEATURE:
<223> OTHER INFORMATION: Synthesized in Lab

<400> SEQUENCE: 28
agcatagcaa gtttaaataa ggctagtccg ttatcaactt gaaaaagtgg caccgagtcg    60
gtgctttttt tggaataaag attgtgtgag cagcctgcat tacctataac caaagctgat   120
tgactgggat gcttt                                                    135

<210> SEQ ID NO 29
<211> LENGTH: 139
<212> TYPE: DNA
```

<213> ORGANISM: Artificial Sequence
<220> FEATURE:
<223> OTHER INFORMATION: Synthesized in Lab

<400> SEQUENCE: 29

```
agcatagcaa gtttaaataa ggctagtccg ttatcaactt gaaaaagtgg caccgagtcg    60
gtgcttttttt tggaataaag attgtgtgag cagcctgcat tacacgatgg taaccaaagc   120
tgattgactg ggatgctttt                                                139
```

<210> SEQ ID NO 30
<211> LENGTH: 141
<212> TYPE: DNA
<213> ORGANISM: Artificial Sequence
<220> FEATURE:
<223> OTHER INFORMATION: Synthesized in Lab

<400> SEQUENCE: 30

```
agcatagcaa gtttaaataa ggctagtccg ttatcaactt gaaaaagtgg caccgagtcg    60
gtgcttttttt tggaataaag attgtgtgag cagcctgcat tacctacgat ggtaaccaaa  120
gctgattgac tgggatgctt t                                              141
```

<210> SEQ ID NO 31
<211> LENGTH: 132
<212> TYPE: DNA
<213> ORGANISM: Artificial Sequence
<220> FEATURE:
<223> OTHER INFORMATION: Synthesized in Lab

<400> SEQUENCE: 31

```
agcatagcaa gtttaaataa ggctagtccg ttatcaactt gaaaaagtgg caccgagtcg    60
gtgcttttttt tggaataaag attgtgtgag cagcctgcga tggtaaccaa agctgattga  120
ctgggatgct tt                                                        132
```

<210> SEQ ID NO 32
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 32

```
agcatagcaa gtttaaataa ggctagccgt tatcaacttg aaaaagtggc accgagtcgg    60
tgcttttttt ggaataaaga ttgtgtgagc agcctgcata cctacgatgg taaccaaagc   120
tgattgactg ggatgctttt                                                139
```

<210> SEQ ID NO 33
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 33

```
agcatagcaa gtttaaataa ggctgtccgt tatcaacttg aaaaagtggc accgagtcgg    60
tgcttttttt ggaataaaga ttgtgtgagc agccgcatta cctacgatgg taaccaaagc   120
tgattgactg ggatgctttt                                                139
```

<210> SEQ ID NO 34
<211> LENGTH: 139

```
<212> TYPE: DNA
<213> ORGANISM: Artificial Sequence
<220> FEATURE:
<223> OTHER INFORMATION: Synthesized in Lab

<400> SEQUENCE: 34
agcatagcaa gtttaaataa ggctagtccg ttatcaactt gaaaaagtgg cacgagtcgg    60 tgctttttt ggaataaaga ttgtgtgagc agcctgcatt acctagatgg taaccaaagc    120
tgattgactg ggatgcttt                                                139

<210> SEQ ID NO 35
<211> LENGTH: 134
<212> TYPE: DNA
<213> ORGANISM: Artificial Sequence
<220> FEATURE:
<223> OTHER INFORMATION: Synthesized in Lab

<400> SEQUENCE: 35
agcatagcaa gtttaaataa ggctagtccg tttcaacttg aaaaagtggc accgagtcgg    60 tgctttttt ggataaagat tgtgtgagca gcctgcatta cctggtaacc aaagctgatt    120
gactgggatg cttt                                                     134

<210> SEQ ID NO 36
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 36
agcatagcaa gtttaaataa ggctagtccg ttatcaactt gaaaaagtgg cacagtcggt    60 gcttttttg gaataaagat tgtgtgagca gcctgcatta cctagatggt aaccaaagct    120
gattgactgg gatgcttt                                                 138

<210> SEQ ID NO 37
<211> LENGTH: 133
<212> TYPE: DNA
<213> ORGANISM: Artificial Sequence
<220> FEATURE:
<223> OTHER INFORMATION: Synthesized in Lab

<400> SEQUENCE: 37
agcatagcaa gtttaaataa ggctagtccg ttatcaactt gaaaaagtgg caccgagtcg    60
gtgctttttt tggaataaag atgtgtgagc agcctgcacg atggtaacca aagctgattg    120
actgggatgc ttt                                                      133

<210> SEQ ID NO 38
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 38
agcatagcaa gtttaaataa ggctagtccg ttatcaactt gaaaaagtgg caccgagcgg    60 tgctttttt ggaataaaga ttgtgtgagc agcctgcatt acctacgtgg taaccaaagc    120
tgattgactg ggatgcttt                                                139
```

<210> SEQ ID NO 39
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 39

```
agcatagcaa gtttaaataa ggctagtccg ttatcaactt gaaaaagtgg caccgagtcg    60 gtgcttttttt tggaataaag attgtgtgag cgcctgcatt acctacgatg gtaaccaagc   120
tattgactgg gatgcttt                                                  138
```

<210> SEQ ID NO 40
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 40

```
agcatagcaa gtttaaataa ggctagtccg tttcaacttg aaaaagtggc accgagtcgg    60 tgctttttttt ggaataaaga ttgtgtgagc agcctgcatt acctagatgg taaccaaagc   120
tgattgactg ggatgcttt                                                 139
```

<210> SEQ ID NO 41
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 41

```
agcatagcaa gtttaaataa ggctagtccg ttatcaacta aaaagtggca ccgagtcggt    60 gcttttttttg gaataaagat tgtgtgagca gctgcattac ctacgatggt aaccaaagct   120
gattgactgg gatgcttt                                                  138
```

<210> SEQ ID NO 42
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 42

```
agcatagcaa gtttaaataa ggctagtccg ttatcaactt gaaaaagtgg caccgagtcg    60 gtgcttttttt tggaataaag attgtgtgag cagcctgcat taccacgatg gtaaccaaag   120
ctgattgact gggatgcttt                                                140
```

<210> SEQ ID NO 43
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 43
agcatagcaa gtttaaataa ggctagtccg ttatcttgaa aaagtggcac cgagtcggtg    60 cttttttttgg aataaagatt gtgtgagcag cctgcattac ctacgatggt aaccaaagct   120
gattgactgg gatgcttt                                                  138

<210> SEQ ID NO 44
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 44
agcatagcaa gtttaaataa ggctagtccg ttatcaactt gaaaaagtgg caccggtcgg    60
tgcttttttt ggaataaaga ttgtgtgaga gcctgcatta cctacgatgg taaccaaagc   120
tgattgactg ggatgcttt                                                 139

<210> SEQ ID NO 45
<211> LENGTH: 141
<212> TYPE: DNA
<213> ORGANISM: Artificial Sequence
<220> FEATURE:
<223> OTHER INFORMATION: Synthesized in Lab

<400> SEQUENCE: 45
agcatagcaa gtttaaataa ggctagtccg ttatcaactt gaaaaagtgg caccgagtcg    60 gtgcttttttt tggaataaag attgtgtgag cagcctgcat tacctacgat ggtaaccaaa   120
gctgattgac tgggatgctt t                                              141

<210> SEQ ID NO 46
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 46
agcatagcaa gtttaaataa ggctagtccg ttatcaactt gaaaaagtgg caccgagtcg    60 gtgcttttttt tggaataaga ttgtgtgagc agcctgcatt acccgatggt aaccaaagct   120
gattgactgg gatgcttt                                                  138

<210> SEQ ID NO 47
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 47
agcatagcaa gtttaaataa ggctagtccg ttatcaactt gaaaaagtgg caccgagtcg    60 gtgcttttttt tggaataaag attgtgtgag cagcctcatt acctacgatg gtaaccaaag   120
ctgattgact gggatgcttt                                                140

<210> SEQ ID NO 48
<211> LENGTH: 139
<212> TYPE: DNA
<213> ORGANISM: Artificial Sequence
<220> FEATURE:

<223> OTHER INFORMATION: Synthesized in Lab

<400> SEQUENCE: 48
agcatagcaa gtttaaataa ggctagtccg ttatcaactt gaaaaagtgg caccgagtcg    60
gtgctttttt tggaataaag attgtgtgag cagcctgcat tacctaatgg taaccaaagc   120
tgattgactg ggatgcttt                                                 139

<210> SEQ ID NO 49
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 49
agcatagcaa gtttaaataa ggctagtccg ttatcaactt gaaaagtggc accgagtcgg    60
tgcttttttt ggaataaaga ttgtgtgagc agcctgcatt acctacgatg gtaaccaaag   120
ctgattgact gggatgcttt                                                140

<210> SEQ ID NO 50
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 50
agcatagcaa gtttaaataa ggctagtccg ttatcaactt gaaaaagtgg cgagtcggtg    60
ctttttttgg aataaagatt gtgtgagcag cctgcattac ctacgatggt aaccaaagct   120
gattgactgg gatgcttt                                                  138

<210> SEQ ID NO 51
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 51
agcatagcaa gtttaaataa ggctagtccg ttatcaactt gaaaaagtgg caccgagtcg    60
gtgctttttt tggaataaag attgtgtgag cagcctgctt acctacgatg gtaaccaaag   120
ctgattgact gggatgcttt                                                140

<210> SEQ ID NO 52
<211> LENGTH: 139
<212> TYPE: DNA
<213> ORGANISM: Artificial Sequence
<220> FEATURE:
<223> OTHER INFORMATION: Synthesized in Lab

<400> SEQUENCE: 52
agcatagcaa gtttaaataa ggctagtccg ttatcaactt gaaaaagtgg caccgagtcg    60
gtgctttttt tggaataaag attgtggagc agcctgcatt actacgatgg taaccaaagc   120
tgattgactg ggatgcttt                                                 139

<210> SEQ ID NO 53
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 53

```
agcatagcaa gtttaaataa ggctagtccg ttatcttgaa aaagtggcac cgagtcggtg    60
ctttttttgg aataaagatt gtgtgagcag cctgcattac ctacgatggt aaccaaagct   120
gattgactgg gatgcttt                                                 138
```

<210> SEQ ID NO 54
<211> LENGTH: 138
<212> TYPE: DNA
<213> ORGANISM: Artificial Sequence
<220> FEATURE:
<223> OTHER INFORMATION: Synthesized in Lab

<400> SEQUENCE: 54

```
agcatagcaa gtttaaataa ggctagtcct tatcaacttg aaaaagtggc accgagtcgg    60
tgcttttttt ggaataaaga ttgtgtgagc agcctgcatc ctacgatggt aaccaaagct   120
gattgactgg gatgcttt                                                 138
```

<210> SEQ ID NO 55
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 55

```
agcatagcaa gtttaaataa ggctagtccg ttatcaactt gaaaaagtgg caccgagtcg    60
tgcttttttt ggaataaaga ttgtgtgagc agcctgcatt acctacgatg gtaaccaaag   120
ctgattgact gggatgcttt                                               140
```

<210> SEQ ID NO 56
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 56

```
agcatagcaa gtttaaataa ggctagtccg ttatcaactt gaaaaagtgg caccgagtcg    60
gtgcttttttt tggaataaag attgtgtgag cagcctgcat tacctagatg gtaaccaaag   120
ctgattgact gggatgcttt                                               140
```

<210> SEQ ID NO 57
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 57

```
agcatagcaa gtttaaataa ggctagtccg ttatcaactt gaaaaagtgg cacgagtcgg    60
tgcttttttt ggaataaaga ttgtgtgagc agcctgcatt acctacgatg gtaaccaaag   120
ctgattgact gggatgcttt                                               140
```

<210> SEQ ID NO 58
<211> LENGTH: 141
<212> TYPE: DNA

<213> ORGANISM: Artificial Sequence
<220> FEATURE:
<223> OTHER INFORMATION: Synthesized in Lab

<400> SEQUENCE: 58

```
agcatagcaa gtttaaataa ggctagtccg ttatcaactt gaaaaagtgg caccgagtcg      60
gtgcttttttt tggaataaag attgtgtgag cagcctgcat tacctacgat ggtaaccaaa    120
gctgattgac tgggatgctt t                                               141
```

<210> SEQ ID NO 59
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 59

```
agcatagcaa gtttaaataa ggctagtccg ttatcaactt gaaaaagtgg caccgagtcg      60
gtgcttttttt tggaataaga ttgtgtgagc agcctgcatt acctacgatg gtaaccaaag    120
ctgattgact gggatgcttt                                                 140
```

<210> SEQ ID NO 60
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 60

```
agcatagcaa gtttaaataa ggctagtccg ttatcaactt gaaaaagtgg caccgagtcg      60
gtgcttttttt tggaataaag attgtgtgag cagcctgcat tacctacgat ggtaaccaag    120
ctgattgact gggatgcttt                                                 140
```

<210> SEQ ID NO 61
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 61

```
agcatagcaa gtttaaataa ggctagtccg ttatcaactt gaaaaagtgg caccgagtcg      60
gtgcttttttt tggaataaag attgtgtgag cagcctgcat tacctacgtg gtaaccaaag    120
ctgattgact gggatgcttt                                                 140
```

<210> SEQ ID NO 62
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 62

```
agcatagcaa gtttaaataa ggctagtccg ttatcaactt gaaaaagtgg caccgagtcg      60
gtgcttttttt tggataaaga ttgtgtgagc agcctgcatt acctacgatg gtaaccaaag    120
ctgattgact gggatgcttt                                                 140
```

<210> SEQ ID NO 63
<211> LENGTH: 140

```
<212> TYPE: DNA
<213> ORGANISM: Artificial Sequence
<220> FEATURE:
<223> OTHER INFORMATION: Synthesized in Lab

<400> SEQUENCE: 63
agcatagcaa gtttaaataa ggctagtccg ttatcaactt gaaaaagtgg caccgagtcg      60 gtgcttttt tggaataaag attgtgtgag cagcctgcat tacctacgat ggtaaccaaa     120
gctgatgact gggatgcttt                                                140

<210> SEQ ID NO 64
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 64
agcatagcaa gtttaaataa ggctagtccg ttatcaactt gaaaaagtgg caccgagtcg      60 gtgcttttt tggaataaag attgtgtgag cagcctgcat acctacgatg gtaaccaaag     120
ctgattgact gggatgcttt                                                140

<210> SEQ ID NO 65
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 65
agcatagcaa gtttaaataa ggctagtccg ttatcaactt gaaaaagtgg caccgagtcg      60 gtgcttttt tggaataaag attgtgtgag cgcctgcatt acctacgatg gtaaccaaag     120
ctgattgact gggatgcttt                                                140

<210> SEQ ID NO 66
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 66
agcatagcaa gtttaaataa ggctagtccg ttatcaactt gaaaaagtgg caccgagtcg      60 gtgcttttt tggaataaag attgtgtgag cagcctgcat tacctacgat ggtaccaaag     120
ctgattgact gggatgcttt                                                140

<210> SEQ ID NO 67
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 67
agcatagcaa gtttaaataa ggctagtccg ttatcaactt gaaaaagtgg caccgagtcg      60 gtgcttttt tggaataaag attgtgtggc agcctgcatt acctacgatg gtaaccaaag     120
ctgattgact gggatgcttt                                                140
```

```
<210> SEQ ID NO 68
<211> LENGTH: 140
<212> TYPE: DNA
<213> ORGANISM: Artificial Sequence
<220> FEATURE:
<223> OTHER INFORMATION: Synthesized in Lab

<400> SEQUENCE: 68
agcatagcaa gtttaaataa ggctagtccg ttatcaactt gaaaaagtgg caccgagtcg      60
gtgctttttt tggaataaag atgtgtgagc agcctgcatt acctacgatg gtaaccaaag    120
ctgattgact gggatgcttt                                                140
```